(12) United States Patent
Kosugi et al.

(10) Patent No.: US 10,264,953 B2
(45) Date of Patent: Apr. 23, 2019

(54) IMAGING APPARATUS

(71) Applicant: Sony Corporation, Tokyo (JP)

(72) Inventors: Hiroshi Kosugi, Kanagawa (JP); Masahito Kikuchi, Tokyo (JP)

(73) Assignee: Sony Corporation, Tokyo (JP)

( * ) Notice: Subject to any disclaimer, the term of this patent is extended or adjusted under 35 U.S.C. 154(b) by 202 days.

(21) Appl. No.: 13/917,043

(22) Filed: Jun. 13, 2013

(65) Prior Publication Data

US 2013/0338439 A1 Dec. 19, 2013

(30) Foreign Application Priority Data

Jun. 19, 2012 (JP) ................. 2012-137459

(51) Int. Cl.
*A61B 1/04* (2006.01)
*A61B 1/00* (2006.01)
*G03B 35/10* (2006.01)

(52) U.S. Cl.
CPC ...... *A61B 1/00193* (2013.01); *A61B 1/00186* (2013.01); *A61B 1/04* (2013.01); *G03B 35/10* (2013.01)

(58) Field of Classification Search
CPC .............. A61B 1/00193; G02B 23/2415
USPC .............................. 600/111, 166
See application file for complete search history.

(56) References Cited

U.S. PATENT DOCUMENTS

| | | | | |
|---|---|---|---|---|
| 5,385,138 A | * | 1/1995 | Berry | A61B 1/00193 359/368 |
| 5,557,454 A | * | 9/1996 | Takahashi | A61B 1/00193 348/45 |
| 5,689,365 A | * | 11/1997 | Takahashi | A61B 1/00179 348/E13.014 |
| 5,864,359 A | * | 1/1999 | Kazakevich | G02B 7/28 348/45 |
| 5,964,696 A | * | 10/1999 | Mihalca | A61B 1/00193 348/45 |
| 2001/0012053 A1 | * | 8/2001 | Nakamura | A61B 1/00193 348/45 |
| 2005/0140820 A1 | * | 6/2005 | Takeuchi | H04N 13/021 348/362 |

(Continued)

FOREIGN PATENT DOCUMENTS

| | | |
|---|---|---|
| JP | 07-020388 | 1/1995 |
| JP | 08-122666 A | 5/1996 |

(Continued)

OTHER PUBLICATIONS

Chinese Office Action dated Feb. 15, 2016 for corresponding Chinese Application No. 201310229337.5.

(Continued)

*Primary Examiner* — Timothy J Neal
*Assistant Examiner* — Jae Woo
(74) *Attorney, Agent, or Firm* — Michael Best & Friedrich LLP

(57) ABSTRACT

An exemplary optical device for stereoscopic imaging that includes an aperture unit. The aperture unite may be configured to adjust an aperture value of first and second aperture portions while maintaining a binocular disparity between a first alignment location of the first aperture portion and a second alignment location of the second aperture portion.

17 Claims, 15 Drawing Sheets

(56) References Cited

U.S. PATENT DOCUMENTS

| | | | |
|---|---|---|---|
| 2012/0206576 A1* | 8/2012 | Sato .................... | G02B 5/3058 348/46 |
| 2012/0212587 A1* | 8/2012 | Otani .................... | G03B 35/10 348/49 |
| 2013/0063569 A1* | 3/2013 | Sato ...................... | G03B 35/08 348/46 |

FOREIGN PATENT DOCUMENTS

| | | |
|---|---|---|
| JP | 10-062697 | 3/1998 |
| JP | 2006-071950 A | 3/2006 |
| JP | 2012-054856 A | 3/2012 |
| WO | 2012/073413 A1 | 7/2012 |

OTHER PUBLICATIONS

Japanese Office Action dated Dec. 1, 2016 for corresponding Japanese Application No. 2012-137459.

* cited by examiner

Baseline length D of binocular disparity

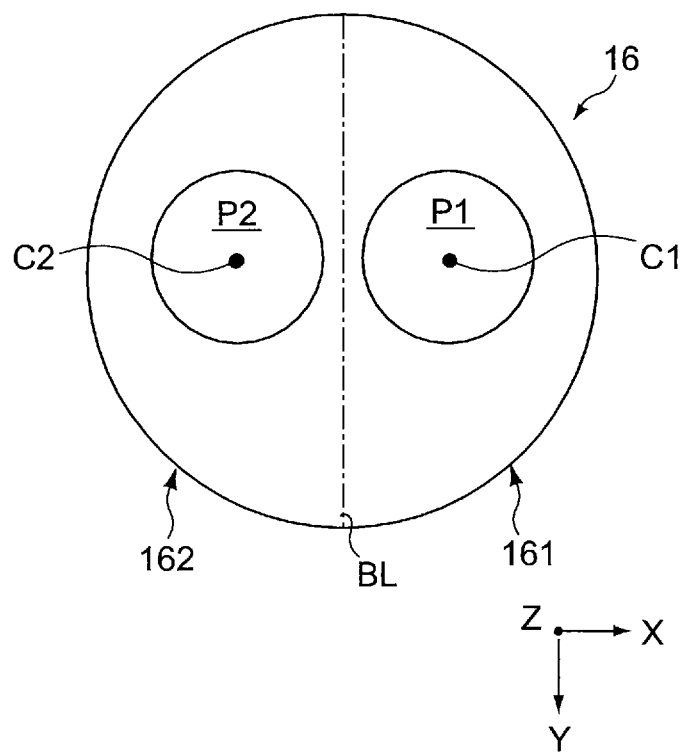

IMAGING APPARATUS

BACKGROUND

The present disclosure relates to an imaging apparatus that images a subject as a stereoscopic image.

For example, in the medical field surgical operations may include observing the procedure through surgical operation is conducted while observing an image captured by an endoscope has been rapidly spread in clinical practice. Thus, there is a growing demand for an endoscope apparatus capable of displaying stereoscopically an affected or a diseased area.

In general, endoscope apparatus examples that image stereoscopically viewable picture may be found in, e.g., see Japanese Patent Application Laid-open No. HEI 07-020388 (hereinafter, referred to as Patent Document 1)). In these exemplary endoscope apparatuses, each type of imaging optical systems capture images having a disparity so that a stereoscopic image may be generated.

Further, Japanese Patent Application Laid-open No. HEI 10-062697 (hereinafter, referred to as Patent Document 2) describes an endoscope apparatus including a lens, a charge-coupled device (CCD), a drum, and a motor. The lens forms an image of an observation site via a diaphragm inside an eyepiece. The CCD includes an imaging surface at an imaging position of the lens. The drum separates the image of the observation site formed by the lens into right and left. The drum supplies the separated image to the imaging surface of the CCD. The motor rotationally drives the drum.

SUMMARY

In view of the above circumstances, disclosed herein is an imaging apparatus capable of obtaining a clear stereoscopic image without increasing the size of the imaging apparatus capable. Further, the imaging apparatus may adjust the depth of field of the image by the diaphragm mechanism.

That is, for example, an optical device for stereoscopic imaging that comprises an aperture unit configured to adjust an aperture value of first and second aperture portions while maintaining a binocular disparity between a first alignment location of the first aperture portion and a second alignment location of the second aperture portion is described herein.

BRIEF DESCRIPTION OF DRAWINGS

FIG. 4 is a schematic plane view showing a main-part configuration of a diaphragm mechanism incorporated in the imaging apparatus;

DETAILED DESCRIPTION OF EMBODIMENTS

Figure 1:
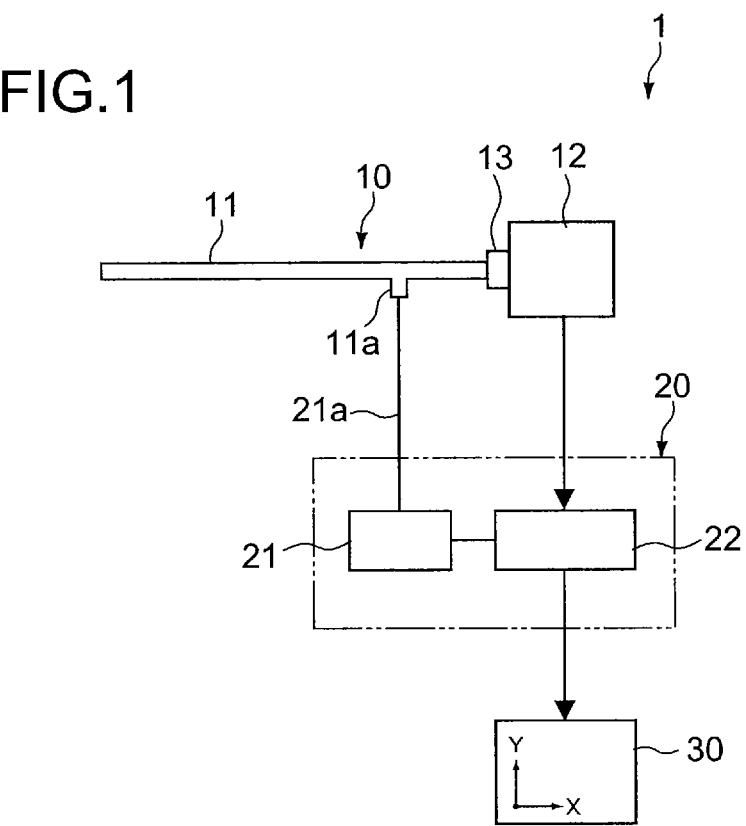
FIG. 1 is a schematic view showing a configuration of an imaging system including an imaging apparatus according to a first embodiment of the present disclosure.

Because the endoscope apparatuses described in Patent Documents 1 and 2 both inevitably increase in size, complexity, and cost, these apparatuses are disadvantageous.

To conduct a correct and rapid endoscope operation while viewing an image of an affected or a diseased area by the use of the endoscope apparatus that provides a stereoscopic view, an endoscope apparatus that provides a clear stereoscopic image without any blur and out-of-focus blur is desirable.

In view of the above, disclosed herein is an imaging apparatus capable of obtaining a clear stereoscopic image without increasing the size of the imaging apparatus capable. Further, the imaging apparatus may adjust the depth of field of the image by the diaphragm mechanism.

For example, an optical device for stereoscopic imaging that comprises an aperture unit configured to adjust an aperture value of first and second aperture portions while maintaining a binocular disparity between a first alignment location of the first aperture portion and a second alignment location of the second aperture portion.

The aperture unit may include a plurality of pairs of the first and the second aperture portions, each pair configured to correspond to a different aperture value, each pair configured to be placed within an optical path to adjust the aperture value to the different aperture value that corresponds to that pair. Each pair of the first and the second apertures may include a polarization filter configured to include first and second filter portions that include a respective first and second mass center, the first filter portion contained within the first aperture portion and the second filter portion contained within the second aperture portion, the first mass center corresponding with the first alignment location and the second mass center corresponding to a second alignment location.

The aperture unit may also include a diaphragm mechanism configured to include the plurality of pairs of the first and the second aperture portions, the diaphragm mechanism being configured to move in a direction orthogonal to the optical path. The diaphragm mechanism may be a plate configured to slide in a direction orthogonal to the optical path. The diaphragm mechanism may be a disk configured to rotate around an axis parallel to the optical path.

The aperture unit may also include a diaphragm mechanism configured to include a pair of movable plates configured to slide along a direction orthogonal to the optical path in opposite directions, wherein the aperture value of the first and the second aperture portions is adjusted based on a position of the pair of movable plates.

The aperture unit may also include a diaphragm mechanism configured to include a pair of iris diaphragms, wherein the aperture value of the first and the second aperture portions is adjusted based on a variable position of the pair of iris diaphragms.

The optical device may also include a polarization filter configured to include first and second filter portions that include a respective first and second mass center, the first mass center corresponding with the first alignment location and the second mass center corresponding to a second alignment location. The polarization filter may be configured on an object side of the aperture unit or an image side of the aperture unit.

In addition, an endoscope apparatus may include a lens barrel, an imaging part, and the optical device as described above.

Hereinafter, embodiments of the present disclosure will be described with reference to the drawings.

First Embodiment

Imaging System

FIG. 1 is a schematic view showing a configuration of an imaging system according to a first embodiment of the present disclosure. In this embodiment, an example of the imaging apparatus applied to an endoscope apparatus used in medical practice will be described.

The imaging system 1 includes an endoscope apparatus 10, a control unit 20, and a monitor 30. Hereinafter, an outline of the imaging system 1 according to this embodiment will be described.

The endoscope apparatus 10 includes a lens barrel 11 and an imaging unit 12. The lens barrel 11 is inserted into a body of a patient and irradiates an affected or a diseased area (subject) with illumination light. The imaging unit 12 receives reflected light (subject light flux) of the affected or the diseased area that is transmitted through the lens barrel 11. The imaging unit 12 converts the received light into an electrical signal and generates an image signal. The imaging unit 12 outputs the generated image signal to the control unit 20.

The control unit 20 includes a light source 21 and a signal processor 22. The light source 21 is connected to a light-source connection 11a of the lens barrel 11 through an optical transmission member 21a, such as optical fibers. The light source 21 introduces the illumination light into the lens barrel 11. The signal processor 22 controls the light source 21 and processes the image signal outputted from the imaging unit 12. The signal processor 22 generates a stereoscopic image (three-dimensional image) of the affected or the diseased area according to the image signal. The signal processor 22 outputs the stereoscopic image to the monitor 30. The monitor 30 includes a display unit (screen).

The display unit has a horizontal direction in an X-axis direction and a vertical direction in a Y-axis direction orthogonal to the X-axis direction. The monitor 30 causes the display unit to display the stereoscopic image of the affected or the diseased area.

Endoscope Apparatus

Next, the endoscope apparatus 10 will be described in detail.

Figure 2:
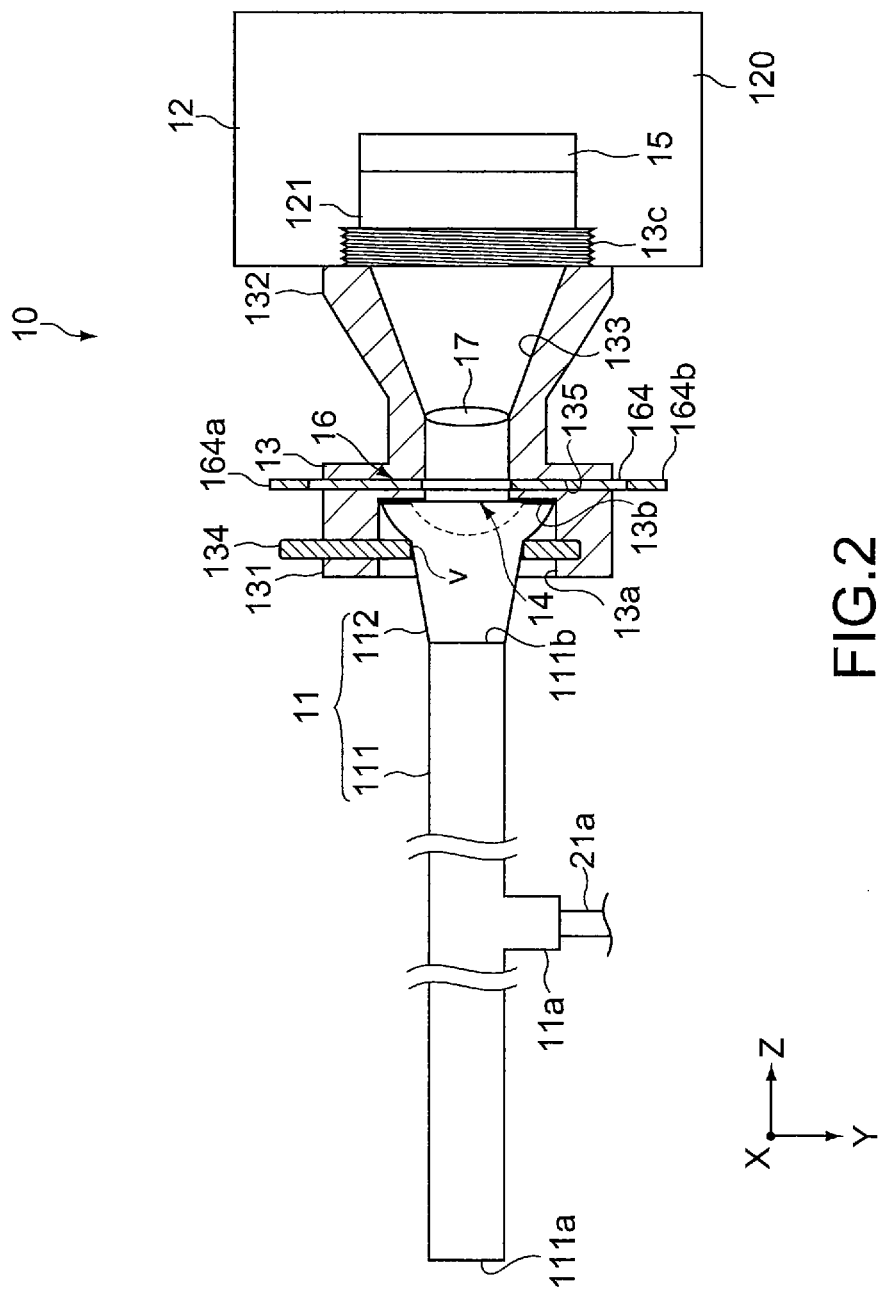
FIG. 2 is a schematic cross-sectional view showing an entire configuration of the imaging apparatus.

FIG. 2 is a schematic cross-sectional view showing an entire configuration of the endoscope apparatus 10. The endoscope apparatus 10 includes the lens barrel 11, the imaging unit 12, and an adapter 13. Note that, in FIG. 2, the X-axis direction indicates a first axis direction. The X-axis direction corresponds to "left- and right-hand directions" of the endoscope apparatus 10. The Y-axis direction indicates a second axis direction orthogonal to the X-axis direction. The Y-axis direction corresponds to "upper and lower directions" of the endoscope apparatus 10. A Z-axis direction indicates a direction orthogonal to each of the X-axis direction and the Y-axis direction.

In FIG. 2, the lens barrel 11 includes a rigid scope 111 and an eyepiece 112. The rigid scope 111 is formed in a cylindrical shape. The rigid scope 111 has a center axis parallel to the Z-axis direction.

The rigid scope 111 includes a distal end portion 111a and a base portion 111b. The distal end portion 111a is inserted into the body of the patient. The base portion 111b is connected to the eyepiece 112. The distal end portion 111a is configured to emit the illumination light and receive the reflected light of the illumination light from the subject. Inside the rigid scope 111, an illumination transmission channel and an imaging optical system 111c (FIG. 3A) are provided. The illumination transmission channel transmits the illumination light introduced into the light-source connection 11a, to the distal end portion 111a. The imaging optical system 111c transmits the subject light flux entering the distal end portion 111a, to the base portion 111b.

The eyepiece 112 is used for a user to directly observe the diseased area. The eyepiece 112 may include an eyepiece lens inside the eyepiece 112. In this embodiment, the imaging optical system 111c is configured such that the position of the subject light flux through the diaphragm corresponds to the position of an eye of the user (doctor or surgical assistant) who directly views the diseased area from the eyepiece 112.

The imaging unit 12 includes a single-plate image sensor 15. The image sensor 15 includes a light-receiving surface. The light-receiving surface receives the subject light flux. The image sensor 15 includes a plurality of pixels arranged along the X-axis direction and the Y-axis direction. For example, the image sensor 15 is constituted of a solid-state image sensor, such as a charge coupled device (CCD) and a complementary metal-oxide semiconductor (CMOS). In the light-receiving surface of the image sensor 15, an array of wire grid polarizers may be formed, as described below.

The imaging unit 12 further includes a casing 120 or the like. The casing 120 houses the image sensor 15. The casing 120 includes an opening portion 121. The opening portion 121 is connected to the adapter 13. The image sensor 15 is provided within the opening portion 121.

The adapter 13 includes a first connection end portion 131, a second connection end portion 132, and a hollow portion 133. The first connection end portion 131 is connected to the eyepiece 112 of the lens barrel 11. The second connection end portion 132 is connected to the opening portion 121 of the imaging unit 12. The adapter 13 connects the eyepiece 112 of the lens barrel 11 to the imaging unit 12. For example, a C-mount adapter is used as the adapter 13.

The adapter 13 is configured to be detachable from the eyepiece 112. With this, a common imaging unit may be used for a plurality types of lens barrels that are different in length and diameter. In this embodiment, the adapter 13 includes a retainer 134. The retainer 134 is attached to the first connection end portion 131 and engageable to the eyepiece 112 by an external operation. The second connection end portion 132 includes a threaded portion 13c. The second connection end portion 132 is connected to the opening portion 121 of the imaging unit 12 through the threaded portion 13c.

As shown in FIG. 2, the first connection end portion 131 of the adapter 13 includes a recess portion 13a. The recess portion 13a may receive an end portion of the eyepiece 112. At a bottom of the recess portion 13a, a reference surface 13b may be formed. The reference surface 13b serves to position the eyepiece 112. When the end portion of the eyepiece 112 abuts against the reference surface 13b, a position of the eyepiece 112 relative to the adapter 13 is defined. The reference surface 13b is formed orthogonal to a Z-axis. The retainer 134 serves to retain the positioned state of the eyepiece 112 with respect to the recess portion 13a. The retainer 134 may be a plate-like member that can be inserted and removed into/from the first connection end portion 131 (recess portion 13a) in the Y-axis direction of FIG. 2 by an external operation. The retainer 134 includes an engagement portion v. The engagement portion v is engaged to an outer peripheral portion of the eyepiece 112 when the retainer 134 is inserted into the recess portion 13a.

The hollow portion 133 is formed to penetrate the adapter 13 in the Z-axis direction. The hollow portion 133 forms a path for introducing the subject light flux emitted from the eyepiece 112, into the image sensor 15. In the hollow portion 133, a polarization filter 14 and an imaging lens 17 are provided. Further, in the adapter 13, an insertion portion 135 is formed to penetrate the hollow portion 133 in the Y-axis direction. A diaphragm mechanism 16 is provided within the insertion portion 135.

The polarization filter 14 includes two filter portions. The two filter portions separate the subject light flux projected from the eyepiece 112, into two polarization components. Specifically, the polarization filter 14 includes a first filter portion 141 and a second filter portion 142 (FIG. 3B). The first filter portion 141 transmits a first polarization component of the subject light flux. The first polarization component oscillates in the X-axis direction. The first filter portion 141 blocks a second polarization component. The second polarization component oscillates in the Y-axis direction. The second filter portion 142 blocks the first polarization component of the subject light flux. The second filter portion 142 transmits the second polarization component.

In this embodiment, the polarization filter 14 is installed in the adapter 13. The polarization filter 14 is provided at the end portion of the eyepiece 112 such that the polarization filter 14 is aligned with the reference surface 13b of the first connection end portion 131. With this, when the adapter 13 is mounted to the eyepiece 112, the polarization filter 14 can be automatically provided in vicinity of the eyepiece 112.

The diaphragm mechanism 16 is inserted into the insertion portion 135 of the adapter 13. The diaphragm mechanism 16 is provided adjacent to a light-emitting side of the polarization filter 14. In this embodiment, the diaphragm mechanism 16 includes a movable plate 164 and a mechanism portion 163. A plurality of openings may be formed in the movable plate 164. The mechanism portion 163 is provided in the insertion portion 135. As described below, the mechanism portion 163 supports the movable plate 164 such that the openings, having different opening areas, may be moved to oppose the polarization filter 14. In turn, an aperture value of the diaphragm mechanism 16 may be adjusted.

The movable plate 164 is configured such that an upper end portion 164a and a lower end portion 164b of the movable plate 164 project from the insertion portion 135 upwards and downwards, respectively. With this, the movable plate 164 may be grasped on an upper end portion 164a or a lower end portion 164b and moved along the Y-axis direction.

The imaging lens 17 is provided between the diaphragm mechanism 16 and the image sensor 15. The imaging lens 17 forms an image of the subject light flux passing through the polarization filter 14 and the diaphragm mechanism 16, on the light-receiving surface of the image sensor 15.

Figure 3A:
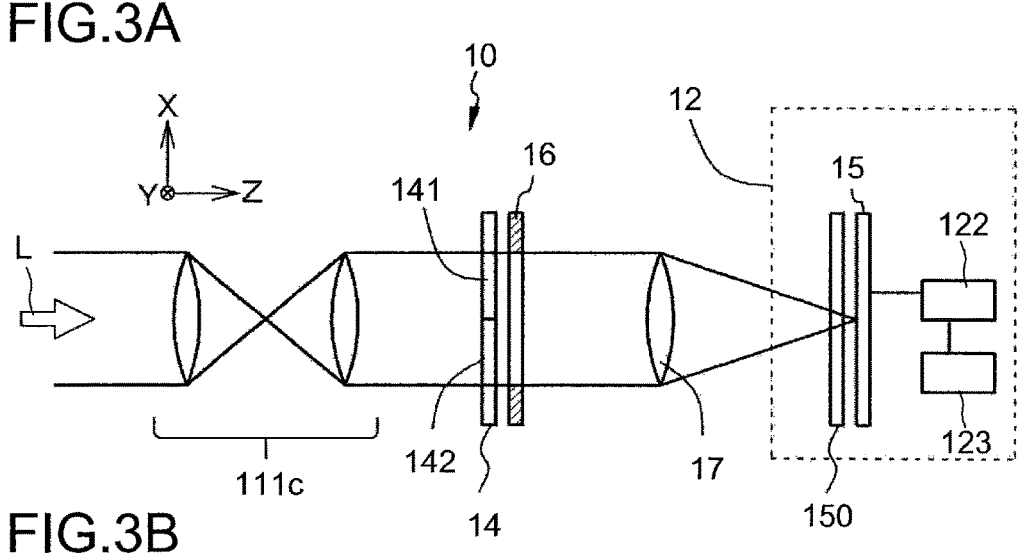
FIG. 3A is a schematic view showing an exemplary optical system of the imaging apparatus.
Figure 3B:
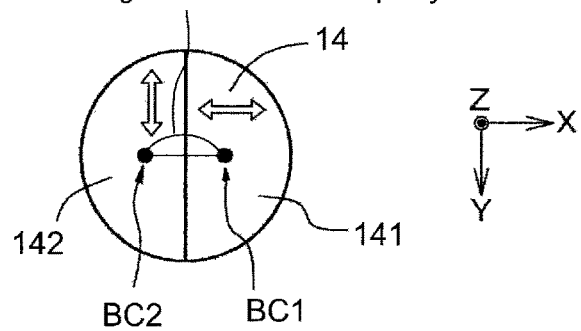
FIG. 3B is a schematic front view of a polarization filter incorporated in the imaging apparatus.

FIG. 3A is a schematic view showing an exemplary optical system of the endoscope apparatus 10.

The imaging optical system 111c includes a focus lens for focusing, a zoom lens for magnifying the subject, and the like. In general, the imaging optical system 111c is constituted of a combination of a plurality of lenses for correcting chromatic aberration and the like. The polarization filter 14 and the diaphragm mechanism 16 are arranged on an optical path of a subject light flux L.

In this embodiment, the diaphragm mechanism 16 is provided at the diaphragm position of the imaging optical system 111c. The subject light flux passing through the diaphragm mechanism 16 becomes parallel light. In addition, the diaphragm mechanism 16 is provided adjacent to the polarization filter 14. Therefore, the diaphragm mechanism 16 may input the subject light flux being the parallel light to the polarization filter 14. With this, it becomes possible to correctly polarize and separate the subject light flux.

FIG. 3B is a front view of the polarization filter 14 as viewed in the Z-axis direction. The polarization filter 14 includes the first filter portion 141 and the second filter portion 142 arranged along the X-axis direction. The first filter portion 141 and the second filter portion 142 may be separated from each other in the left- and right-hand directions of the display unit of the monitor 30. The first filter portion 141 polarizes the subject light flux in the X-axis direction. The second filter portion 142 polarizes the subject light flux in the Y-axis direction. Thus, a polarization state of first polarized light L1 passing through the first filter portion 141 and a polarization state of second polarized light L2 passing through the second filter portion 142 are different from each other.

FIG. 4 is a main-part front view of the diaphragm mechanism 16 as viewed in the Z-axis direction. FIG. 4 shows an area of the diaphragm mechanism 16 opposed to the polarization filter 14. As described below, when the diaphragm mechanism 16 moves in the Y-axis direction, the area of the diaphragm mechanism 16 opposed to the polarization filter 14 also changes. Thus, the aperture value may be changed. FIG. 4 shows an exemplary area of the diaphragm mechanism 16 opposed to the polarization filter 14. Further, the line BL of FIG. 4 indicates a boundary line corresponding to a boundary line between the first filter portion 141 and the second filter portion 142 of the polarization filter 14.

The diaphragm mechanism 16 includes a first opening portion P1 and a second opening portion P2. The first opening portion P1 is opposed to the first filter portion 141. The second opening portion P2 is opposed to the second filter portion 142. In this embodiment, a center C1 of the first opening portion P1 and a center C2 of the second opening portion P2 are opposed to a gravity center BC1 (natural center or mass center) of the first filter portion 141 and a gravity center BC2 (natural center or mass center) of the second filter portion 142 in the Z-axis direction, respectively. With this, the first opening portion P1 and the second opening portion P2 cause the first polarized light L1 containing light passing through the gravity center BC1 and the second polarized light L2 containing light passing through the gravity center BC2 to pass through the first opening portion P1 and the second opening portion P2, respectively. Alternatively, the first and the second opening portions P1, P2 may contain modified versions of the first filter portion 141 and the second filter portion 142 of the polarization filter 14. In this case, the center C1 of the first opening portion P1 and the center C2 of the second opening portion P2 would correspond (e.g., be the same point as) the gravity center BC1 (natural center or mass center) of the first filter portion 141 and the gravity center BC2 (natural center or mass center) of the second filter portion 142, respectively.

Figure 3C:
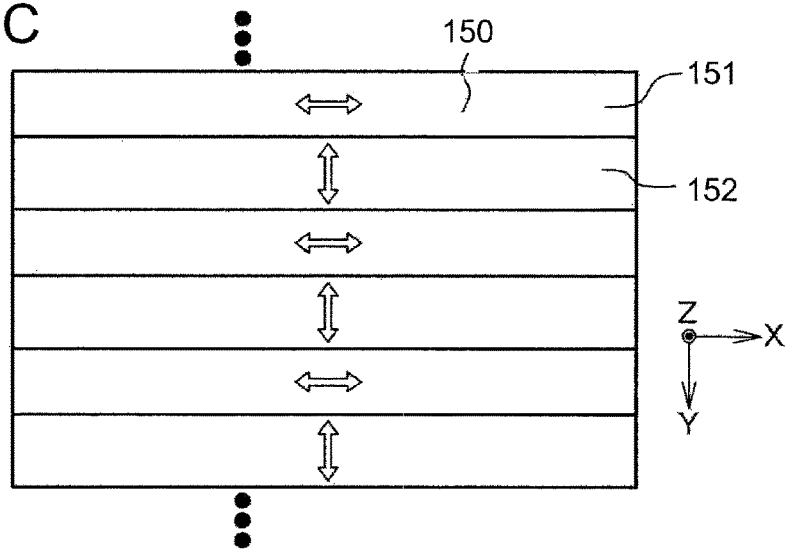
FIG. 3C is a schematic view showing a light-receiving surface of an image sensor incorporated in the imaging apparatus.

FIG. 3C is a schematic view showing light-receiving surfaces 150 of the image sensor 15. The light-receiving surfaces 150 are alternately arranged along the Y-axis direction (along vertical direction or along upper and lower directions). The light-receiving surfaces 150 include a plurality of first polarization areas 151 and a plurality of second polarization areas 152. The first polarization areas 151 and the second polarization areas 152 extend in the X-axis direction (in horizontal direction or in left- and right-hand directions). The first polarization areas 151 transmit the first polarized light L1 that oscillates in the X-axis direction. The first polarization areas 151 block the second polarized light L2 of the subject light flux that oscillates in the Y-axis direction. The second polarization areas 152 block the first polarized light L1 that oscillates in the X-axis direction. The second polarization areas 152 transmit the second polarized light L2 of the subject light flux that oscillates in the Y-axis direction. Thus, the first polarized light L1 passes through the first polarization areas 151 and arrives at the image sensor 15. The second polarized light L2 passes through the second polarization areas 152 and arrives at the image sensor 15.

The image sensor 15 captures images for obtaining a stereoscopic image having a baseline length D of a binocular disparity. Here, the baseline length D is set at a distance between the gravity center BC1 of the first filter portion 141 and the gravity center BC2 of the second filter portion 142. The imaging unit 12 includes, in addition to the image sensor 15, for example, an image processor 122 and an image storage unit 123.

The image processor 122 converts the first polarized light L1 and the second polarized light L2 arriving at the image sensor 15 into electrical signals. Thus, the image processor 122 generates right-eye image data (first disparity image data) from the first polarized light L1 and generates left-eye image data (second disparity image data) from the second polarized light L2. Such image data may be stored in the image storage unit 123. Note that, the image processor 122 and the image storage unit 123 may be provided in the signal processor 22 of the control unit 20.

The polarization filter 14 has a circular outer shape. The first filter portion 141 and the second filter portion 142 each have a semicircular outer shape occupying a half of the polarization filter 14. The boundary line between the first filter portion 141 and the second filter portion 142 extends in the Y-axis direction. The polarization filter 14 constituted of a combination of the two filter portions separates incident light into two different polarization states.

As described above, the polarization filter 14 is constituted of the left-right symmetrical polarizers. At two left and right positions in an erected state of the endoscope apparatus 10, the polarization filter 14 generates straight polarized light beams orthogonal to each other or generates polarized light beams in opposite rotation directions. The first filter portion 141 may a filter that polarizes an image of the subject to be viewed by a right eye (light to be received by right eye). The second filter portion 142 may be a filter that polarizes an image of the subject to be viewed by a left eye (light to be received by left eye).

In this embodiment, the polarization filter 14 has a circular outer shape having a radius r of 10 mm. Further, the first filter portion 141 and the second filter portion 142 each have a semicircular shape occupying the half of the polarization filter 14. Thus, a distance D between the gravity center BC1 of the first filter portion 141 and the gravity center BC2 of the second filter portion 142 is $[(8r)/(3\pi)]=8.5$ mm.

The polarizer constituting the polarization filter 14 is not particularly limited. For example, a reflection type polarization plate may be used. The reflection type polarization plate has a structure in which an organic multi-layer film having different refraction indexes is stacked on a glass plate. Alternatively, a wire grid polarizer, a polarizer that performs polarization and separation with inorganic particles having optical anisotropy, an organic polarization film, or the like may be used.

As a method of assembling the first filter portion 141 and the second filter portion 142, the following method is exemplified. In this method, two semicircular polarization plates made of left and right polarizers are formed. Those polarization plates are combined together along their straight lines to have a circular shape. The combined polarization plates are sandwiched between two glass plates or the like. With this, the polarization filter 14 having two areas having different polarization directions can be easily manufactured. Alternatively, the following method may also be used. In this method, an area, in which one filter portion is created, is masked on a circular glass plate or the like. A multi-layer film is deposited (or similarly formed) in an area that is to be the other filter portion. Then, the multi-layer film is masked, and the other filter portion is deposited or the like. This method omits the process of combining the two polarization plates. In FIG. 3B, a direction of an electric field of the first polarized light L1 (indicated by an arrow) is orthogonal to a direction of an electric field of the second polarized light L2 (indicated by another arrow). Here, the direction of the electric field of the first polarized light L1 is parallel to the X-axis direction. Specifically, for example, the first polarized light L1 mainly has a P-wave (transverse magnetic (TM) wave) as the polarization component. The second polarized light L2 mainly has an S-wave (transverse electric (TE) wave) as the polarization component.

In addition, as shown in FIG. 3C, the direction of the electric field of the first polarized light L1 is parallel to the direction of the electric field of the first polarization areas 151 (indicated by an arrow). The direction of the electric field of the second polarized light L2 is parallel to the direction of the electric field of the second polarization areas 152 (indicated by another arrow). Further, an extinction ratio of each polarizer is 3 or more, more favorably, 10 or more.

Figure 5:
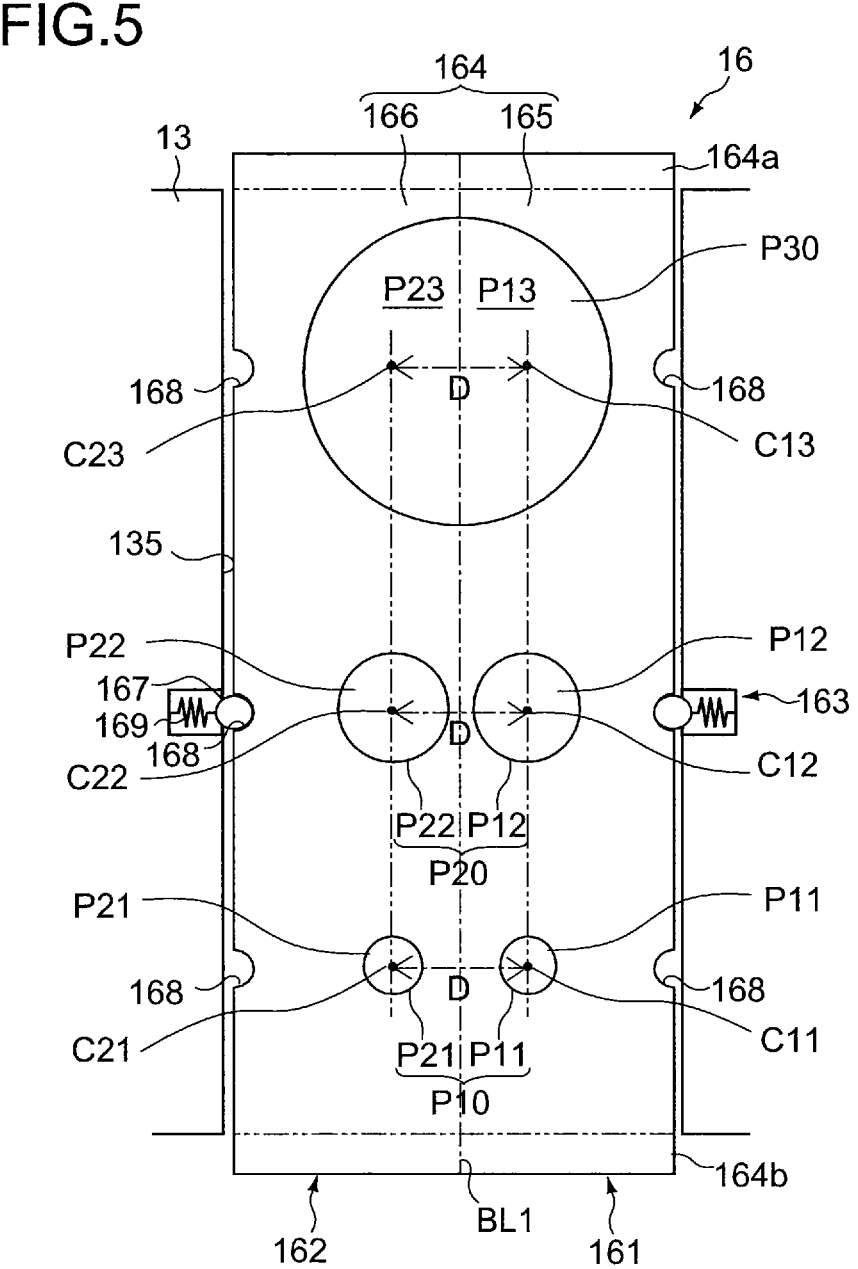
FIG. 5 is a schematic plane view showing a configuration of the diaphragm mechanism.

FIG. 5 is a front view showing an entire configuration of the diaphragm mechanism 16 as viewed in the Z-axis direction. The diaphragm mechanism 16 includes a first diaphragm portion 161 and a second diaphragm portion 162. The first diaphragm portion 161 is opposed to the first filter portion 141. The second diaphragm portion 162 is opposed to the second filter portion 142. The diaphragm mechanism 16 changes the aperture value of the first diaphragm portion 161 and the second diaphragm portion 162.

The first diaphragm portion 161 adjusts a subject depth (aperture value) with respect to the image of the subject to be viewed by the right eye (image light for right eye). Similarly, the second diaphragm portion 162 adjusts a subject depth (aperture value) with respect to the image of the subject to be viewed by the left eye (image light for left eye).

The depth of field is a distance range on a side of the subject where a captured image appears to be in focus. A relationship between the depth of field and the aperture value is generally as follows. That is, as the aperture value becomes larger, the depth of field becomes deeper. As the aperture value becomes smaller, the depth of field becomes shallower.

In the diaphragm mechanism 16 according to this embodiment, by the movable plate 164 moving along the Y-axis direction, the openings having different opening areas are opposed to the polarization filter 14. Alternatively, the opening areas may contain modified versions of the polarization filter 14. With this, the aperture value of the first diaphragm portion 161 and the second diaphragm portion 162 changes, and the depth of field is adjusted. Note that, "increasing the aperture value" corresponds to reducing the opening area of the opening portion and "reducing the aperture value" corresponds to increasing the opening area of the opening portion.

The first diaphragm portion 161 includes a plurality of right opening portions (first opening portions) P11, P12, and P13 and a right plate portion (first plate portion) 165. The right opening portions P11, P12, and P13 transmit image light for the right eye. The second diaphragm portion 162 includes a plurality of left opening portions (second opening portions) P21, P22, and P23 and a left plate portion (second plate portion) 166. The left opening portions P21, P22, and P23 transmit image light for the left eye. The right opening portions P11, P12, and P13 and the left opening portions P21, P22, and P23 are arranged in the right plate portion 165 and the left plate portion 166 along the Y-axis direction, respectively.

The right plate portion 165 and the left plate portion 166 may be integrally formed. The right plate portion 165 and the left plate portion 166 constitute the movable plate 164. In other words, the right plate portion 165 and the left plate portion 166 constitute a right half area and a left half area of the single movable plate 164, respectively. In this embodiment, the movable plate 164 is a black rectangular plate. With this, it becomes possible to block light in the area of the movable plate 164 other than the opening portions. Note that, a boundary line BL1 indicated by the alternate long and short dash line of FIG. 5 is a virtual line showing the boundary between the first diaphragm portion 161 and the second diaphragm portion 162 (right plate portion 165 and left plate portion 166). When the boundary line BL1 is projected to the polarization filter 14 in the Z-axis direction, the boundary line BL1 corresponds to the boundary line between the first filter portion 141 and the second filter portion 142.

In addition, the movable plate 164 includes the upper end portion 164*a* and the lower end portion 164*b*. As described above, the upper end portion 164*a* and the lower end portion 164*b* are configured to project from the adapter 13 upwards and downwards, respectively. Further, a plurality of notches 168, which are described below, are connected at left and right ends of the right plate portion 165 and the left plate portion 166, along the Y-axis direction. The notches 168 are at positions opposed to the right opening portions P11, P12, and P13 and the left opening portions P21, P22, and P23 in the X-axis direction.

The right opening portion P11 and the left opening portion P21 of the plurality of opening portions are circular openings having the same opening area. The right opening portion P11 and the left opening portion P21 are spaced from each other in the X-axis direction. The right opening portion P11 and the left opening portion P21 constitute a first opening pair P10. Similarly, the right opening portion P12 and the left opening portion P22 are circular openings having the same opening area. The right opening portion P12 and the left opening portion P22 are spaced from each other in the X-axis direction. The right opening portion P12 and the left opening portion P22 constitute a second opening pair P20.

Further, a distance between a center C11 of the right opening portion P11 and a center C21 of the left opening portion P21 is the baseline length D of the binocular disparity. Similarly, a distance between a center C12 of the right opening portion P12 and a center C22 of the left opening portion P22 is also D.

On the other hand, the right opening portion P13 and the left opening portion P23 constitute a right semicircular area and a left semicircular area of a circular opening P30. Further, a distance between a gravity center C13 (natural center or mass center) of the right opening portion P13 and a gravity center C23 (natural center or mass center) of the left opening portion P23 is also D.

In this embodiment, the opening portions P12 and P22 of the second opening pair P20 have an opening area larger than that of the opening portions P11 and P21 of the first opening pair P10. In addition, the opening portions P13 and P23 that constitute the opening P30 have an opening area larger than that of the opening portions P12 and P22 of the second opening pair P20. With this, the amount of light of the subject light flux passing through the opening P30, the second opening pair P20, and the first opening pair P10 is reduced in the stated order. The aperture value becomes larger in this order. Note that, the opening area of the opening is not particularly limited as long as a desired aperture value can be achieved. For example, when the image sensor 15 has a size of ½ inches, the opening P30 has an opening diameter of about 8 mm. When the image sensor 15 has a size of ⅓ inches, the opening P30 has an opening diameter of about 5 mm.

In the movable plate 164, the first opening pair P10, the second opening pair P20, and the opening P30 are arranged along the Y-axis direction. With this, by moving the movable plate 164 in the Y-axis direction, any one of the first opening pair P10, the second opening pair P20, and the opening P30 can be opposed to the polarization filter 14.

More specifically, in the movable plate 164, the centers C11, C12, and C13 of the right opening portions P11, P12, and P13 and the centers C21, C22, and C23 of the left opening portions P21, P22, and P23 are arranged along the Y-axis direction in equal intervals, respectively. With this, by moving the movable plate 164 in the Y-axis direction, any one of the centers C11, C12, and C13 can be opposed to the gravity center BC1 of the first filter portion 141 in the Z-axis direction. At the same time, any one of the centers C21, C22, and C23 can be opposed to the gravity center BC2 of the second filter portion 142 in the Z-axis direction.

In this embodiment, the diaphragm mechanism 16 is inserted into the insertion portion 135 of the adapter 13 along the Y-axis direction. The mechanism portion 163 supports manipulation of the movable plate 164 (right plate portion 165 and left plate portion 166) with respect to the insertion portion 135 along the Y-axis direction. That is, the mechanism portion 163 supports the movable plate 164 such that any one of the right opening portions P11, P12, and P13 may oppose the first filter portion 141 while any one of the left opening portions P21, P22, and P23 may oppose the second filter portion 142. With this, the diaphragm mechanism 16, aperture value of the subject light flux and can adjust the brightness, and the depth of field of the right-eye image and the left-eye image.

The mechanism portion 163 includes, for example, left and right engagement portions 167, the plurality of notches 168, and the left and right spring members 169. The left and right engagement portions 167 may be engaged to the notches 168 opposed to each other in the left- and right-hand directions. The plurality of notches 168 are in the movable plate 164. The left and right spring members 169 are attached to the insertion portion 135. The left and right spring members 169 can bias the left and right engagement portions 167 against any of the notches 168. That is, by the notches 168 being engaged to the left and right engagement portions 167 at a position corresponding to any of the first opening pair P10, the second opening pair P20, and the opening P30, the mechanism portion 163 can define a position of the diaphragm mechanism 16 relative to the insertion portion 135 (adapter 13) and maintain the relative position. For example, as shown in FIG. 5, when the notches 168 and the left and right engagement portions 167 corresponding to the second opening pair P20 are engaged to each other, the second opening pair P20 is placed to be opposed to the polarization filter 14.

For example, by the engagement portions 167 being biased by the spring members 169 against the notches 168, the engagement portions 167 support the movable plate 164. With this structure, when a predetermined force or more is applied to the movable plate 164 in the Y-axis direction, the engagement state between the engagement portions 167 and the notches 168 is released. Then, the engagement portions 167 can be further engaged to the other notches 168. That is, by the user grasping the upper end portion 164a or the lower end portion 164b of the movable plate 164 and moving the movable plate 164, it is possible to set the aperture value of the diaphragm mechanism 16 to be a desired aperture value.

Note that, the upper end portion 164a and the lower end portion 164b may be machined into a shape easy for the user to grasp. For example, the upper end portion 164a and the lower end portion 164b may each have a finger hole or the like. Further, the upper end portion 164a and the lower end portion 164b may each have a recessed surface.

Figure 6A:
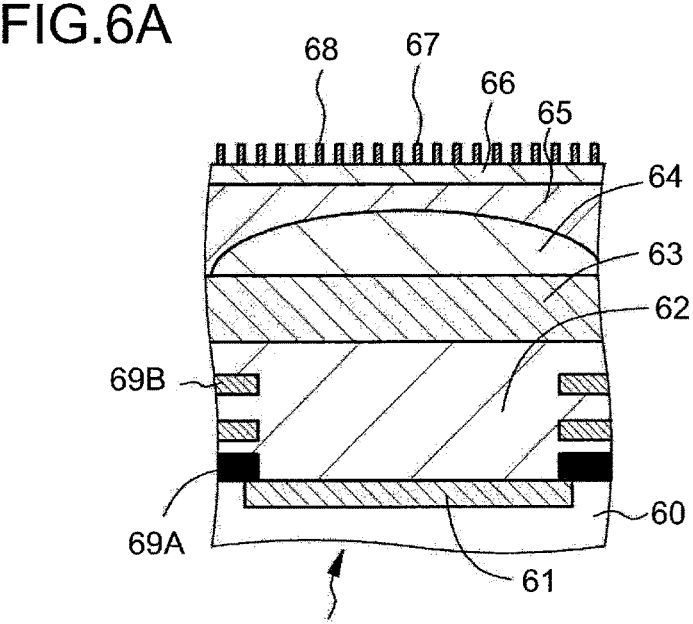
FIG. 6A is a cross-sectional view schematically showing a configuration of the image sensor and FIG. 6B is a schematic view showing the light-receiving surface of the image sensor.
Figure 6B:
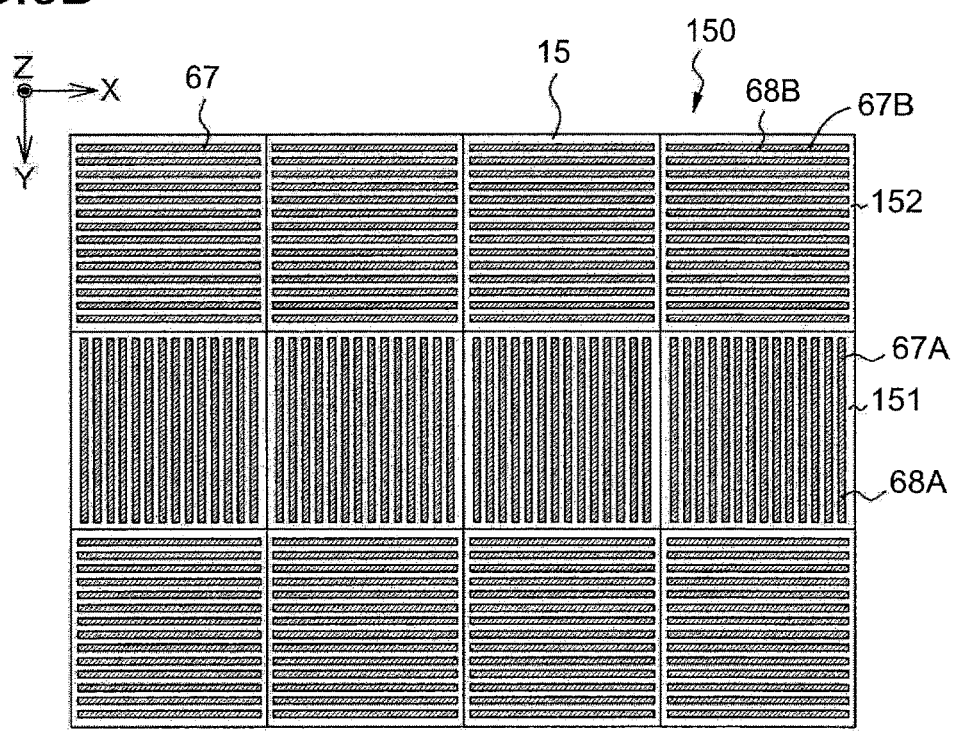

The first polarization areas 151 and the second polarization areas 152 arranged in the light-receiving surfaces 150 of the image sensor 15 are constituted of the wire grid polarizers. FIG. 6A is a cross-sectional view schematically showing a configuration of the image sensor 15. FIG. 6B is a front view as viewed in the Z-axis direction and schematically shows an arrangement state of the first polarization areas 151 and the second polarization areas 152.

The image sensor 15 has the following structure, for example. Specifically, the image sensor 15 includes a photoelectric conversion element 61 provided on a silicon semiconductor substrate 60. The image sensor 15 further includes a first planar film 62, a color filter 63, an on-chip lens 64, a second planar film 65, an inorganic insulation base layer 66, and wire grid polarizers 67. The first planar film 62, the color filter 63, the on-chip lens 64, the second planar film 65, the inorganic insulation base layer 66, and the wire grid polarizers 67 are stacked above the photoelectric conversion element 61. The wire grid polarizers 67 constitute each of the first polarization areas 151 and the second polarization areas 152. In FIG. 6B, boundary areas between pixels are indicated be the solid lines.

A direction in which a plurality of wires 68 constituting the wire grid polarizers 67 extend is parallel to the X-axis direction or the Y-axis direction. Specifically, regarding wire grid polarizers 67A constituting the first polarization areas 151, the direction in which the wires 68A extend is parallel to the Y-axis direction. Regarding wire grid polarizers 67B constituting the second polarization areas 152, the direction in which the wires 68B extend is parallel to the X-axis direction. A direction orthogonal to the direction in which the wires 68 extend serves as a light transmission axis in the wire grid polarizers 67.

In this embodiment, the first polarized light L1 passes through the first polarization areas 151 and arrives at the image sensor 15. An electrical signal for obtaining right-eye image data is generated in the image sensor 15 from the first polarized light L1. Further, the second polarized light L2 passes through the second polarization areas 152 and arrives at the image sensor 15. An electrical signal for obtaining left-eye image data is generated in the image sensor 15 from the second polarized light L2. The image sensor 15 outputs those electrical signals at the same time or alternately in a time series. The image processor 122 executes image processing on the outputted electrical signals (electrical signals for right-eye image data and left-eye image data outputted from image sensor 15). Then, the right-eye image data and the left-eye image data are stored in the image storage unit 123.

Figure 7A:
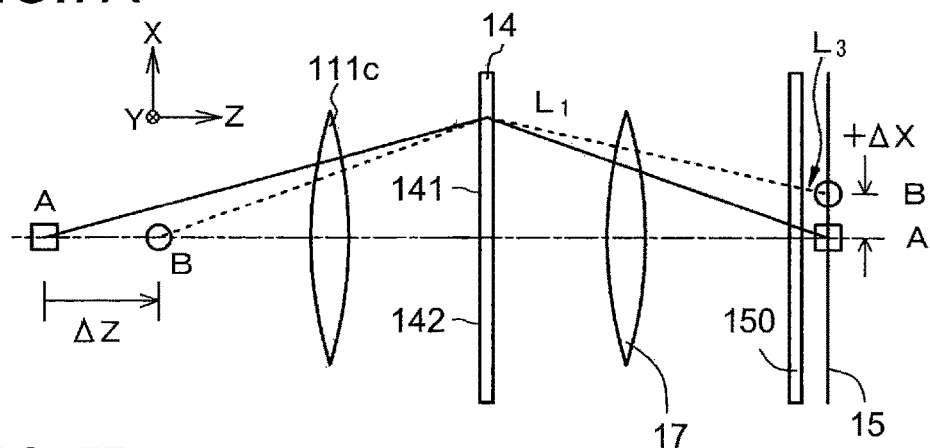
FIGS. 7A and 7B are conceptual views of light traveling from the subject to the image sensor and FIGS. 7C and 7D are views schematically showing an image formed in the image sensor from the light shown in FIGS. 6A and 6B.
Figure 7B:
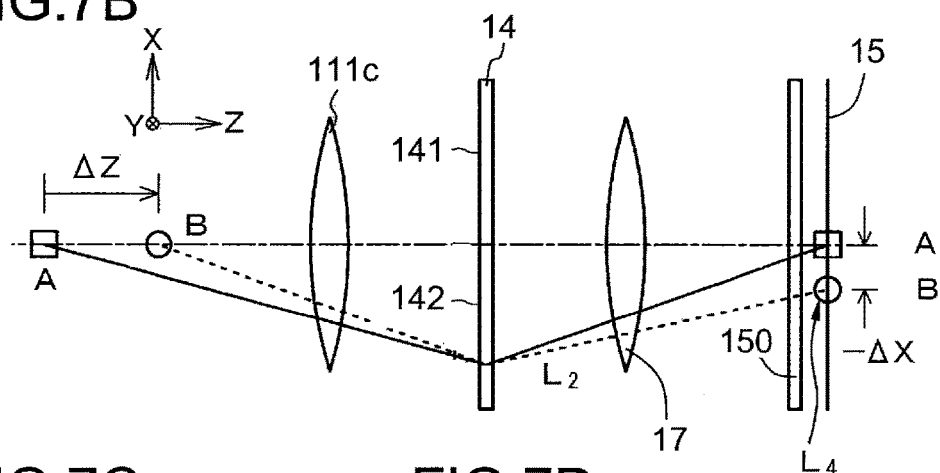
Figure 7C:
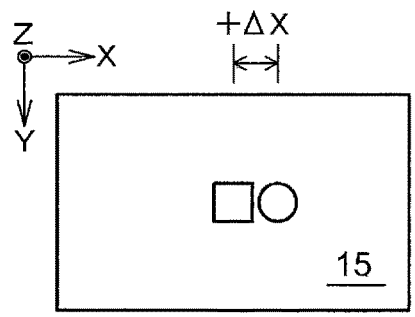
Figure 7D:
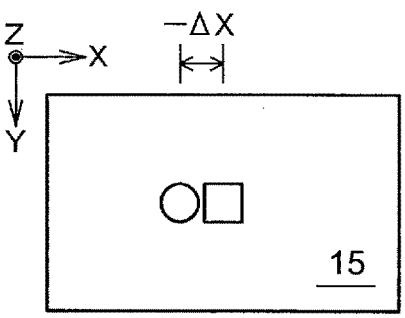

FIGS. 7A and 7B are conceptual views of light traveling from the subject to the image sensor 15 through the diaphragm mechanism 16. FIGS. 7C and 7D are views each schematically showing an image received on the image sensor from the light shown in FIGS. 7A and 7B.

As schematically shown in FIGS. 7A and 7B, it the imaging optical system 111c is in focus on a rectangular object A. Further, a circular object B is positioned closer to the imaging optical system 111c than the object A. Light L1 and light L2 are reflected on the object A and the object B. The light L1 and light L2 pass through the center C1 of the first opening portion P1 and the center C2 of the second opening portion P2 of the diaphragm mechanism 16. The light L1 and light L2 arrive at the image sensor 15. An image of the rectangular object A is received on the image sensor 15 in a focused state. Further, an image of the circular object B is received on the image sensor 15 in an unfocused state.

In the example of FIG. 7A, on the image sensor 15, the light L1 (first polarized light) reflected by the object B forms an image at a position spaced from the object B on a right-hand side of the object A by a distance ($+\Delta X$). On the other hand, in the example of FIG. 7B, on the image sensor 15, the light L2 (second polarized light) reflected by the object B forms an image at a position spaced from the object B on a left-hand side of the object A by a distance ($-\Delta X$). Thus, a distance ($2 \times \Delta X$) serves as information on the depth of the object B. That is, the amount of blur and the direction of blur of the object B positioned closer to the endoscope apparatus than the object A are different from the amount of blur and the direction of blur of the object positioned further from the endoscope apparatus. The amount of blur of the object B varies depending on a distance between the object A and the object B.

With this, from the first polarized light L1 passing through the first opening portion P1 and the second polarized light L2 passing through the second opening portion P2, the right-eye image (see the schematic view of FIG. 7C) and the left-eye image (see the schematic view of FIG. 7D) that are different from each other maybe obtained. Then, from the right- and left-eye images, the stereoscopic image may be generated. Also, by mixing the right-eye image data with the left-eye image data, not the stereoscopic image but a normal two-dimensional (plane) image may be generated.

Figure 8:
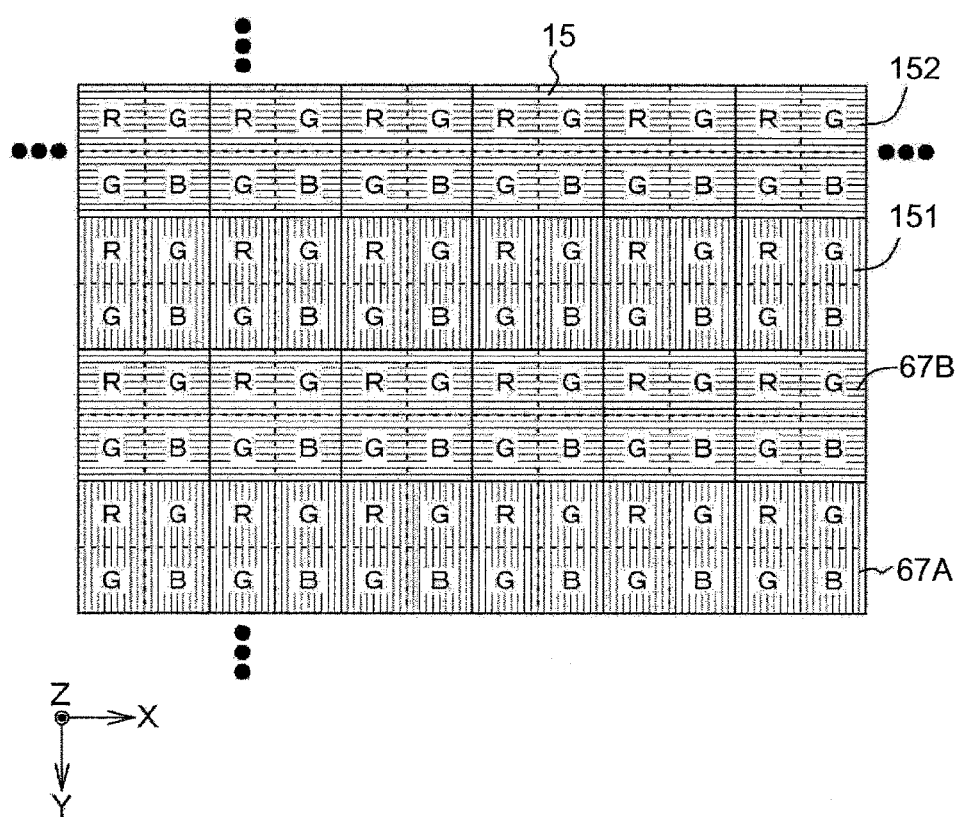
FIG. 8 is a conceptual view explaining the light-receiving surface of the image sensor.

FIG. 8 is a conceptual view explaining the light-receiving surface of the image sensor 15.

The image sensor 15 includes a Bayer array. One pixel includes four sub-pixels (one red pixel R that receives red light, one blue pixel B that receives blue light, and two green pixels G that receive green light). The first polarization area 151 is provided for a group of pixels arranged along the X-axis direction, the group of pixels corresponding to one column of pixels. Similarly, the second polarization area 152 are provided for a group of pixels arranged along the X-axis direction, the group of pixels corresponding to one column of pixels and being adjacent to the former group of pixels. The first polarization areas 151 and the second polarization areas 152 are alternately arranged along the Y-axis direction.

The first polarization areas 151 and the second polarization areas 152 extend in the X-axis direction as a whole. A unit length of the first polarization areas 151 and the second polarization areas 152 along the X-axis direction and the Y-axis direction is equal to the length of the image sensor 15 along the X-axis direction and the Y-axis direction. With this configuration, a band-like image (right-eye image) and a band-like image (left-eye image) are alternately generated along the Y-axis direction. The band-like image (right-eye image) extends in the X-axis direction and is based on light mainly containing a P-wave component. The band-like image (left-eye image) extends in the X-axis direction and is based on light mainly containing an S-wave component. In FIG. 8, the first polarization areas 151 have vertical lines and the second polarization areas 152 have horizontal lines. Those lines schematically express the wires of the wire grid polarizers 67A and 67B.

As described above, the electrical signals for the right-eye image data and the electrical signals for the left-eye image data are generated on alternate lines along the Y-axis direction. For generating the right-eye image data and the left-eye image data, the image processor 122 generates the right-eye image data and the left-eye image data by performing mosaic processing and, for example, ultra-resolution processing on the electrical signals. Further, for example, a disparity detection technique and a disparity control technique may be utilized to emphasize and optimize the disparity. In the disparity detection technique, a disparity map is generated from the left-eye image data and the right-eye image data by stereo matching. In the disparity control technique, the disparity is controlled based on the disparity map.

Figure 9:
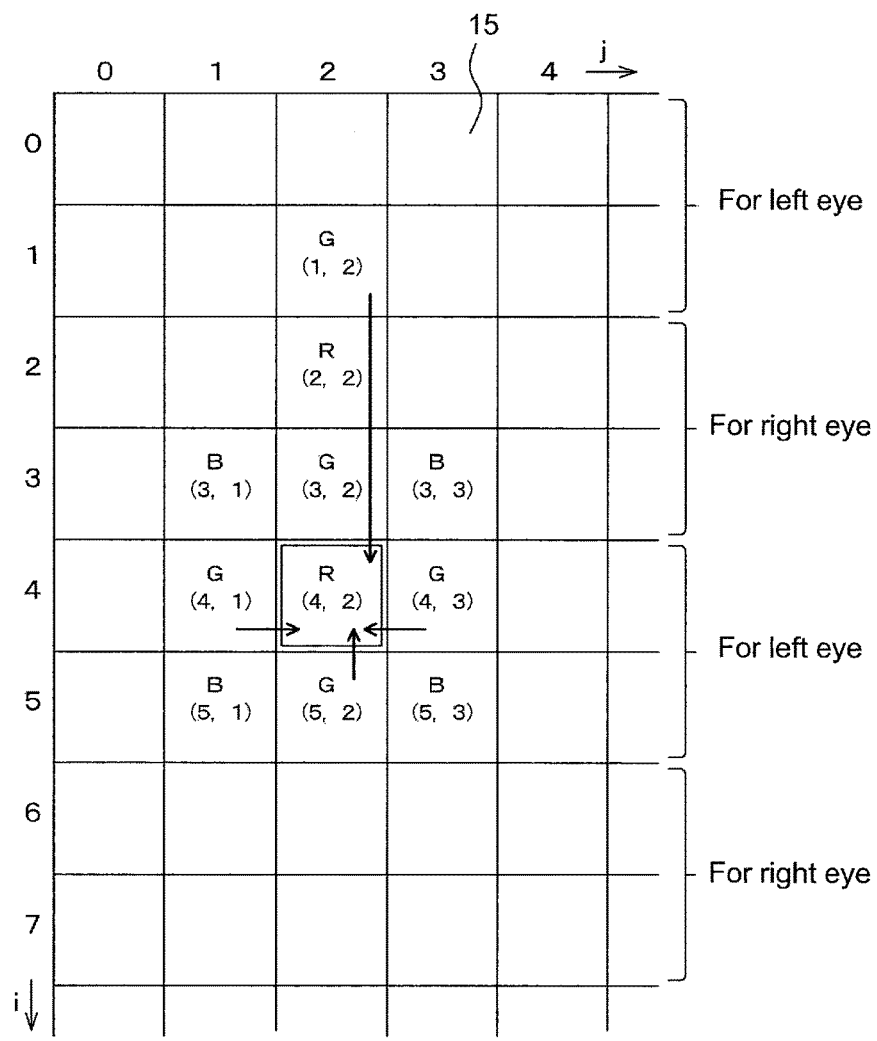
FIG. 9 shows a conceptual view explaining the light-receiving surface of the image sensor.

FIG. 9 shows a conceptual view of the light-receiving surface including a Bayer array for explaining image processing (mosaic processing). In the image processing, mosaic processing is performed on the electrical signals obtained from the image sensor and signal values are obtained. FIG. 9 shows an example in which a signal value of a green pixel of the left-eye image is generated.

In typical demosaic processing, an average value of electrical signals of the same-color pixels is used, the same-color pixels being located near each other. However, as in this embodiment, in the case where the pixel group (pixel row) for obtaining the right-eye image data and the pixel group (pixel row) for obtaining the left-eye image data are alternately repeated, if the values located near each other are used as they are, there is a fear that original image data cannot be obtained. Therefore, the demosaic processing is performed considering whether an electrical signal of a pixel to be referred to belongs to the right-eye image data or the left-eye image data.

In a Bayer array, it is assumed that the red pixel R is located at a position (4,2). At this time, to generate a green-pixel signal value g' corresponding to the position (4,2), calculation may be performed by the following equation:

$$g'4,2=(g4,1+g4,3+g5,2+g1,2\times W3)/(3.0+W3), \quad \text{Equation (1)}$$

where, g'i,j as a left-hand member represents the green-pixel signal value at the position (i,j). Further, gi,j as a right-hand member represents a value of an electrical signal of a green pixel at the position (i,j). In addition, "3.0" corresponds to the sum of weights assuming that a distance (W1) between a target pixel G4,2 and each of adjacent pixels G4,1, G4,3, and G5,2 is, for example, "1.0" and a multiplicative inverse of each distance is a weight. Similarly, W3 is a weight on a value of an electrical signal of a pixel G1,2 spaced from the target pixel G4,2 by three pixels. In this case, W3 is "⅓." The following equation is obtained by generalizing the above equation.

Thus, in the case where i is an even number (signal value of the green pixel G corresponding to the position of the red pixel R):

$$g'i,j=(gi,j-1\times W1+gi,j+1\times W1+gi+1,j\times W1+gi-3,j\times W3)/(W1\times 3.0+W3). \quad \text{Equation (2)}$$

In the case where i is an odd number (signal value of the green pixel G corresponding to the position of the blue pixel B):

$$g'i,j=(gi,j-1\times W1+gi,j+1\times W1+gi-1,j\times W1+gi+3,j\times W3)/(W1\times 3.0+W3), \quad \text{Equation (3)}$$

where W1=1.0 and W3=⅓.

Also regarding the red pixel R and the blue pixel B, mosaic processing may be performed based on a similar concept.

Although the demosaic processing may obtain the pixel signal value at each pixel position, at this phase, the pixel signal values are arranged on alternate lines as described above. Therefore, pixel signal values in an area having no pixel signal values may be generated by supplement (complement). Further, a method of using an arithmetic mean value of values located near each other may also be utilized. The supplement processing may be performed in parallel to the demosaic processing. Thus, image quality is completely maintained in the X-axis direction, and hence image quality deterioration, such as reduced resolution of the entire image, is relatively small.

According to this embodiment, two different images separated into left and right by the polarization filter 14 may be generated at the same time. The stereoscopic image of the affected or the diseased area may be obtained with a single lens. Further, a small-size endoscope apparatus 10 having simple configuration and structure and including a small number of components may be provided. Further, a plurality of combinations of the lens and the polarization filter are replaced, and hence an offset and a difference are not caused in a zoom, an aperture stop, a focus, a convergence angle, or the like. In addition, when the polarization filter 14 is detachable from the adapter 13, it is possible to easily obtain a two-dimensional image and a three-dimensional image.

Further, the endoscope apparatus 10 according to this embodiment includes the diaphragm mechanism 16, and hence it becomes possible to change the aperture value and maintain the binocular disparity between the right-eye image and the left-eye image. Hereinafter, referring to FIGS. 10A to 10C and FIGS. 11A to 11C, actions of the diaphragm mechanism 16 according to this embodiment are described.

Figure 10A:
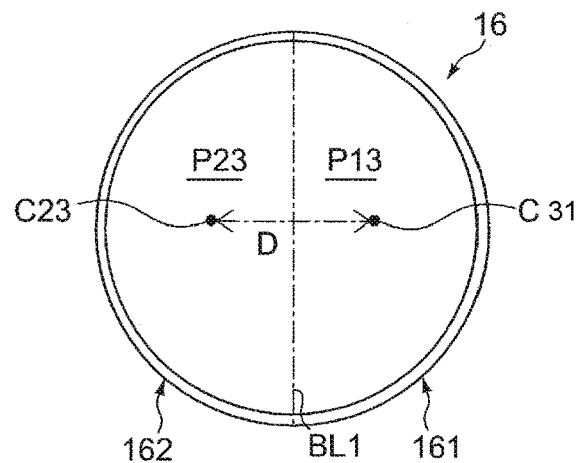
FIGS. 10A to 10C are schematic plane views showing a main-part configuration of the diaphragm mechanism, each of which shows a state of the diaphragm mechanism adjusted to have a different aperture value.
Figure 10B:
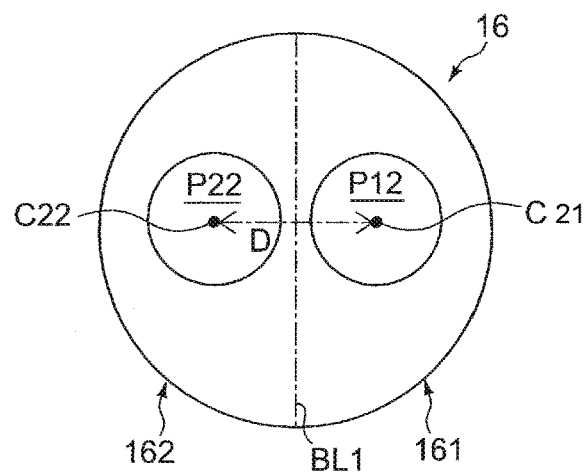
Figure 10C:
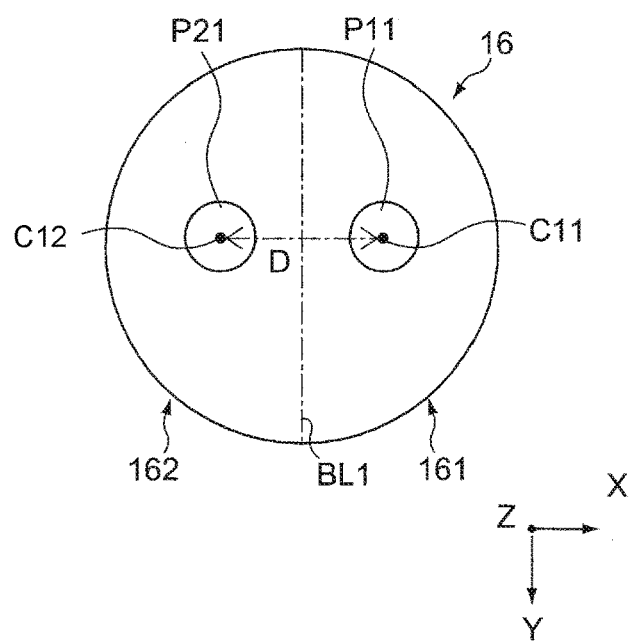

FIGS. 10A to 10C each are a main-part front view of the diaphragm mechanism 16 as viewed in the Z-axis direction and shows an area overlapping with the polarization filter 14. Further, FIGS. 10A to 10C show states in which the diaphragm mechanism 16 has different aperture values.

FIG. 10A shows a first opening state in which the opening P30 is opposed to the polarization filter 14. In the first opening state, the aperture value of the diaphragm mechanism 16 is the smallest, that is, the diaphragm is opened to the maximum degree. The amount of light of the subject light flux is the maximum. Further, the depth of field is the shallowest. Further, a distance between a gravity center C31 (natural center or mass center) and a gravity center C32 (natural center or mass center) is the distance D between gravity center (natural center or mass center) positions of the first filter portion 141 and the second filter portion 142.

FIG. 10B shows a second opening state in which the second opening pair P20 is opposed to the polarization filter 14. In the second opening state, the aperture value of the diaphragm mechanism 16 is smaller than in the first opening state. The amount of light of the subject light flux is smaller than in the first opening state. The depth of field is deeper than in the first opening state. Further, a distance between the center C21 and the center C22 is D.

FIG. 10C shows a third opening state in which the first opening pair P10 is opposed to the polarization filter 14. In the third opening state, the aperture value of the diaphragm mechanism 16 is the largest. The amount of light of the subject light flux is the smallest. Further, the depth of field is the deepest. Further, a distance between the center C11 and the center C12 is D.

As described above, in the first to third opening states, both of the distance between the centers of the first opening pair P10 and the second opening pair P20 and the distance between the center positions of the opening P30 correspond to the distance D between the center positions of the first filter portion 141 and the second filter portion 142. Further, the first polarized light L1 emitted from the first filter portion 141 surely passes through any one of the centers C11, C12, and C13. The second polarized light L2 emitted from the second filter portion 142 surely passes through any one of the centers C21, C22, and C23. That is, regarding the right-eye image data generated from the first polarized light L1 and the left-eye image data generated from the second polarized light L2, the baseline length of the binocular disparity is maintained at D irrespective of the aperture value.

Figure 11A:
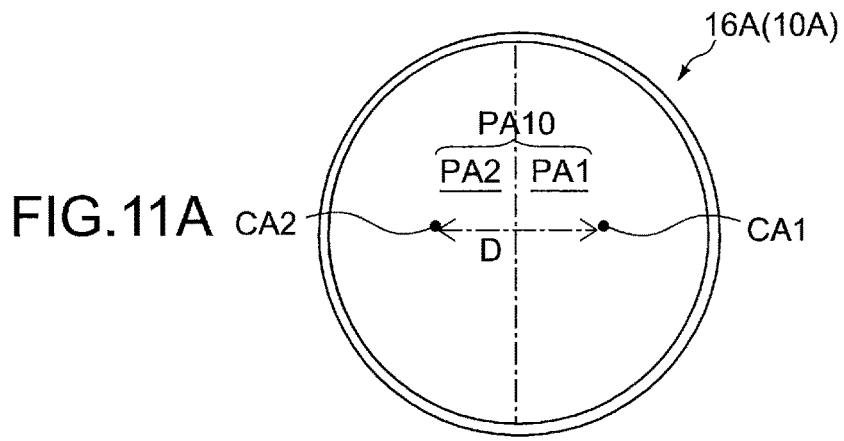
FIG. 11A to 11C are schematic plane views showing a main-part configuration of a diaphragm mechanism according to a reference example of the first embodiment, each of which shows a state of the diaphragm mechanism adjusted to have a different aperture value.
Figure 11B:
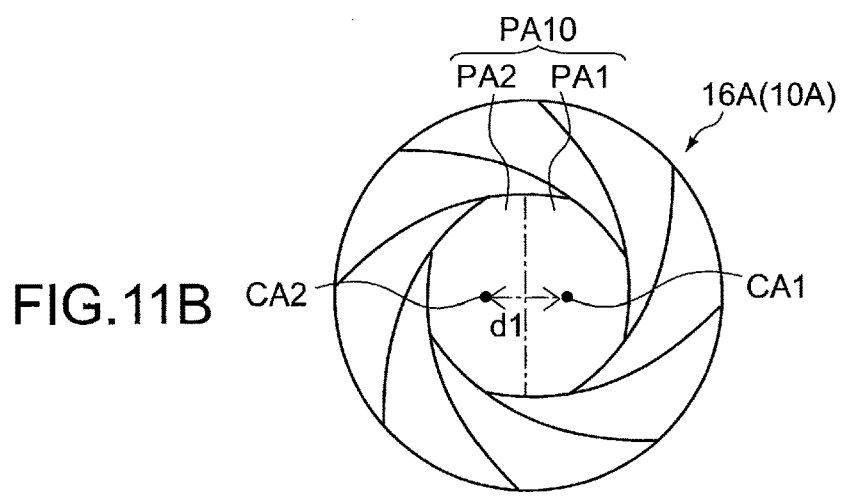
Figure 11C:
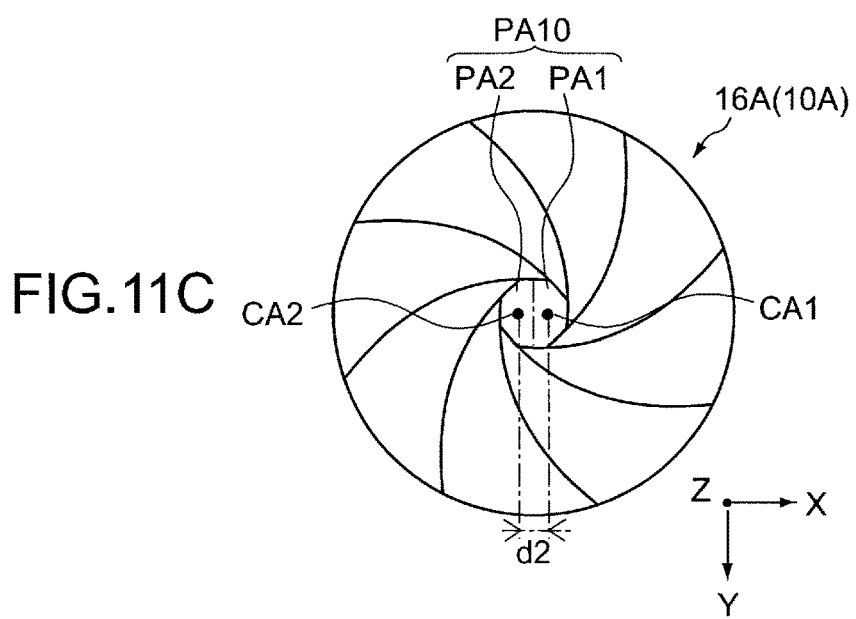

On the other hand, FIGS. 11A to 11C are views explaining an endoscope apparatus 10A obtained by adding a diaphragm mechanism 16A to the endoscope apparatus 10 instead of the diaphragm mechanism 16. FIGS. 11A to 11C are main-part front views of the diaphragm mechanism 16A as viewed in the Z-axis direction.

The diaphragm mechanism 16A is constituted of an iris diaphragm with a plurality of (e.g., eight) plates (diaphragm blades) overlapping with each other. The diaphragm mechanism 16A includes one opening PA10 having a variable opening area. The diaphragm mechanism 16A includes a right opening portion PA1 opposed to the first filter portion 141 and a left opening portion PA2 opposed to the second filter portion 142.

FIG. 11A shows a fourth opening state in which the aperture value of the opening PA10 is the smallest, that is, the diaphragm is opened to the maximum degree. In the fourth opening state, the opening PA10 is structured in a circular shape having the same size as that of the opening P30. The distance between the centers of the right opening portion PA1 and the left opening portion PA2 is D. Therefore, the baseline length of the binocular disparity of the stereoscopic image captured by the endoscope apparatus 10A is maintained at D.

FIG. 11B shows a fifth opening state in which the opening diameter of the opening PA10 is smaller and the aperture value is larger than in the fourth opening state. In the fifth opening state, the opening PA10 has an almost octagonal shape with diaphragm blades. The amount of light of the subject light flux can be smaller and the depth of field can be deeper than in the fourth opening state. A distance between a center CA1 of the right opening portion PA1 and a center CA2 of the left opening portion PA2 is d1 smaller than D.

FIG. 11C shows a sixth opening state in which the aperture value of the opening PA10 is larger than in the fifth opening state. In the sixth opening state, with the opening PA10, the amount of light of the subject light flux can be further smaller and the depth of field can be further deeper than in the fifth opening state. A distance between the center CA1 of the right opening portion PA1 and the center CA2 of the left opening portion PA2 is d2 further smaller than D and d1.

As described above, also with the diaphragm mechanism 16A, it becomes possible to adjust the brightness and the depth of field of the right-eye image and the left-eye image obtained from the first polarized light L1 and the second polarized light L2. On the other hand, the diaphragm mechanism 16A includes the one opening PA10, and hence a distance between the gravity center CA1 of the right opening portion PA1 and the gravity center CA2 (natural center or mass center) of the left opening portion PA2 decreases in proportion to the opening diameter. With this, the baseline length of the binocular disparity also decreases in proportion to the opening diameter.

That is, in the endoscope apparatus 10A, the baseline length of the binocular disparity between the right-eye image and the left-eye image decreases in proportion to the opening diameter. Thus, in the case where the opening diameter is reduced as in the fifth opening state and the sixth opening state, it is difficult to generate a stereoscopic image having a desired disparity.

In contrast, in the diaphragm mechanism 16 according to this embodiment, both of the distance between the centers of the first opening pair P10 and the distance between the centers of the second opening pair P20 correspond to the distance D between the center positions of the first filter portion 141 and the second filter portion 142. Therefore, even when the size of the opening of the diaphragm is reduced, the baseline length of the binocular disparity is maintained at D. With this, it becomes possible to change the aperture value and maintain a desired binocular disparity. Therefore, according to this embodiment, it is possible to provide the endoscope apparatus 10 capable of adjusting the depth of field without deteriorating a stereoscopic effect.

Second Embodiment

Figure 12:
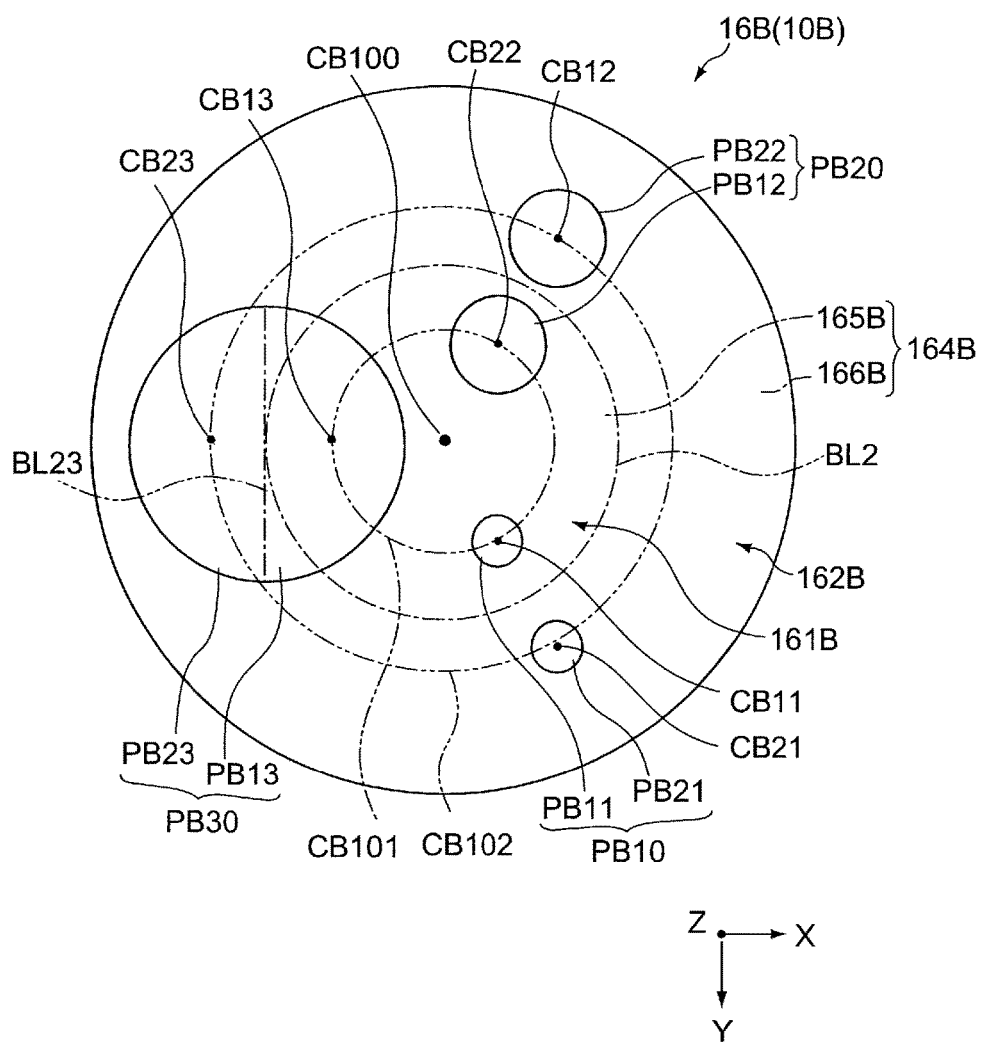
FIG. 12 is a schematic plane view showing a configuration of the diaphragm mechanism according to a second embodiment of the present disclosure.

FIG. 12 is a view showing a configuration of a diaphragm mechanism 16B in an endoscope apparatus 10B according to a second embodiment of the present disclosure. FIG. 12 is a front view as viewed in the Z-axis direction. Note that, in FIG. 12, parts corresponding to those of the above-mentioned first embodiment will be denoted by the same reference symbols and detailed description will be omitted or simplified.

In this embodiment, in the diaphragm mechanism 16B, by a disk-like movable plate 164B rotating around the Z-axis, an opening having a different opening area is opposed to the polarization filter 14. Alternatively, the opening areas may contain modified versions of the polarization filter 14. With this, the aperture value of a first diaphragm portion 161B and a second diaphragm portion 162B is changed.

In this embodiment, the movable plate 164B is a disk-like shape having a center CB100. The movable plate 163B comprises two areas including a circular inner-peripheral plate portion 165B (first plate portion), which includes the center CB100, and an annular outer-peripheral plate portion 166B (second plate portion) provided around the inner-peripheral plate portion 165B. That is, the inner-peripheral plate portion 165B and the outer-peripheral plate portion 166B are integrated. The inner-peripheral plate portion 165B and the outer-peripheral plate portion 166B constitute the movable plate 164B. Further, a boundary line BL2 indicated by the alternate long and short dash line of FIG. 12 is a virtual line showing a boundary between a first diaphragm portion 161B and a second diaphragm portion 162B (first plate portion 165B and second plate portion 166B). The boundary line BL2 passes through almost a center of the polarization filter 14 when the boundary line BL2 is projected to the polarization filter 14.

The first diaphragm portion 161B includes a plurality of inner-peripheral opening portions (first opening portions) PB11, PB12, and PB13 and the inner-peripheral plate portion 165B. The plurality of inner-peripheral opening portions PB11, PB12, and PB13 and the inner-peripheral plate portion 165B are along a first circumference CB101. The second diaphragm portion 162B includes outer-peripheral opening portions (second opening portions) PB21, PB22, and PB23 and the outer-peripheral plate portion 166B. The outer-peripheral opening portions PB21, PB22, and PB23 and the outer-peripheral plate portion 166B are along a second circumference CB102. The inner-peripheral opening portions PB11, PB12, and PB13 all transmit a right-eye image light. The outer-peripheral opening portions PB21, PB22, and PB23 all transmit a left-eye image light.

Out of the plurality of opening portions, the inner-peripheral opening portion PB11 and the outer-peripheral opening portion PB21 are circular openings having the same opening area. The inner-peripheral opening portion PB11 and the outer-peripheral opening portion PB21 are separated from each other in a radial direction. The inner-peripheral opening portion PB11 and the outer-peripheral opening portion PB21 constitute a first opening pair PB10. Similarly, the inner-peripheral opening portion PB12 and the outer-peripheral opening portion PB22 are circular openings having the same opening area. The inner-peripheral opening portion PB12 and the outer-peripheral opening portion PB22 are separated from each other in the radial direction. The inner-peripheral opening portion PB12 and the outer-peripheral opening portion PB22 constitute a second opening pair PB20. The inner-peripheral opening portion PB13 and the outer-peripheral opening portion PB23 constitute semicircular inner and outer peripheral areas on a circular opening PB30. Note that, a boundary line BL23 indicated by the alternate long and short dash line shows a boundary between the inner-peripheral opening portion PB13 and the outer-peripheral opening portion PB23. When the opening PB30 is opposed to the polarization filter 14, the boundary line BL23 is a virtual line opposed to the boundary line between the first filter portion 141 and the second filter portion 142 in the Z-axis direction.

Centers CB11 and CB12 of the inner-peripheral opening portions PB11 and PB12 and a gravity center CB13 (natural center or mass center) of the inner-peripheral opening portion PB13 are arranged on the first circumference CB101. Similarly, centers CB21 and CB12 of the outer-peripheral opening portions PB21 and PB22 and a gravity center CB23 (natural center or mass center) of the outer-peripheral opening portion PB23 are arranged on the second circumference CB102. The first circumference CB101 and the second circumference CB102 are virtual concentric circles with the center CB100 being a center. The first circumference CB101 and the second circumference CB102 are indicated by the alternate long and two short dashes line of FIG. 12. Further, a difference between those radii is the distance D between the center positions of the first filter portion 141 and the second filter portion 142. With this, a distance between the centers of the first opening pair PB10 and a distance between the centers of the second opening pair PB20 and a distance between the center positions of the opening PB30 are all D. The baseline length D of the binocular disparity is maintained.

As in the first embodiment, the opening portions PB21 and PB22 of the second opening pair PB20 have an opening area larger than the opening portions PB11 and P21 of the first opening pair PB10. In addition, the opening portions PB13 and P23 constituting the opening PB30 have an opening area larger than the opening portions PB21 and P22 of the second opening pair PB20. With this, the amount of light passing through the opening PB30, the second opening pair PB20, and the first opening pair PB10 is reduced in the stated order. The aperture value increases in this order. That is, the depth of field of an image becomes deeper in this order.

In this embodiment, the mechanism portion (not shown) is configured to move the movable plate 164B along the first circumference CB101 and the second circumference CB102. The mechanism portion moves the inner-peripheral plate portion 165B and the outer-peripheral plate portion 166B such that any one of the inner-peripheral opening portions PB11, PB12, and PB13 is opposed to the first filter portion 141 and any one of the outer-peripheral opening portions PB21, PB22, and PB23 is opposed to the second filter portion 142. With this, the aperture value of the subject light flux can be adjusted and the brightness and the depth of field of the right-eye image and the left-eye image can be adjusted.

For example, the mechanism portion may be constituted of a reducer that rotates and stops the movable plate 164B about the Z-axis. For example, the reducer is provided with an output shaft. The output shaft passes through the center CB100 of the movable plate 164B. The reducer rotates or stops the output shaft. A worm reducer or the like may be used as the reducer. The reducer may also be driven by an electric motor or the like. With this, the mechanism portion may be driven without directly touching the endoscope apparatus 10B.

Further, the first opening pair PB10, the second opening pair PB20, and the opening PB30 may be at equal intervals about the center CB100. With this, for switching among the first opening pair PB10, the second opening pair PB20, and the opening PB30, the movable plate 164B may be rotated by equal angles (120°).

Also with the endoscope apparatus 10B according to this embodiment having the above-mentioned configuration, the same actions and effects as those of the above-mentioned first embodiment can be given. That is, the diaphragm mechanism 16B includes the plurality of opening pairs PB10 and PB20 with the distance between the centers being maintained at D. It becomes possible to change the aperture value and maintain the binocular disparity.

Third Embodiment

Figure 13A:
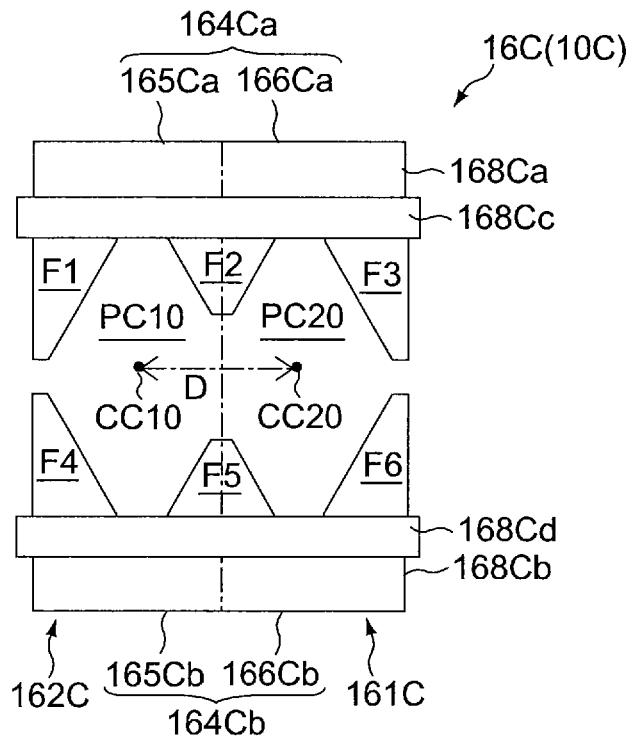
FIGS. 13A and 13B are schematic plane view each showing a configuration of a diaphragm mechanism according to a third embodiment of the present disclosure.
Figure 13B:
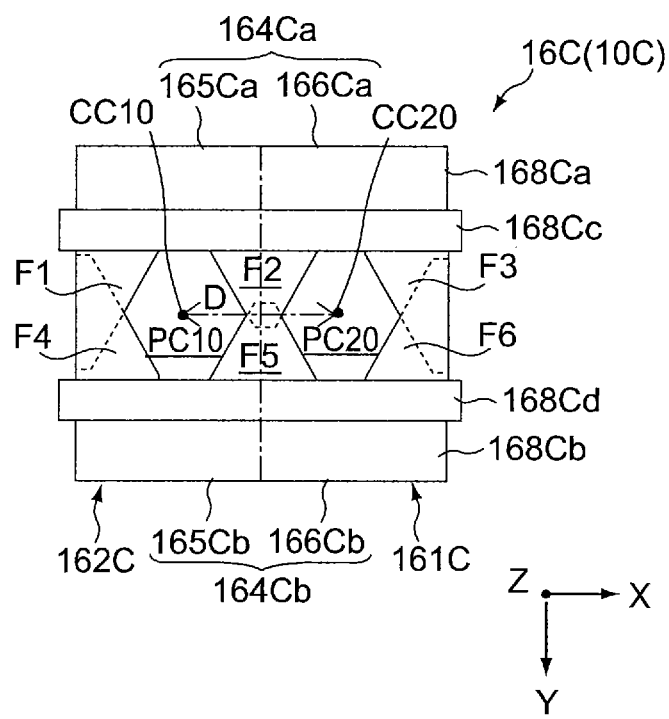

FIGS. 13A and 13B are views each showing a configuration of a diaphragm mechanism 16C in an endoscope apparatus 10C according to a third embodiment of the present disclosure. FIGS. 13A and 13B are front views as viewed in the Z-axis direction. Note that, in FIGS. 13A and 13B, parts corresponding to those of the above-mentioned first embodiment will be denoted by the same reference symbols and detailed description will be omitted or simplified.

In this embodiment, the diaphragm mechanism 16C includes a pair of movable plates 164Ca and 164Cb in the Y-axis direction. A right opening portion PC10 (first opening portion) and a left opening portion PC20 (second opening portion) are formed between and by the pair of movable plates 164Ca and 164Cb.

A first diaphragm portion 161C includes a pair of plate portions 165Ca and 165Cb (first pair of plate portions) on a right-hand side. By overlapping with each other, the pair of plate portions 165Ca and 165Cb may form the right opening portion PC10 opposed to the first filter portion 141. Also, a second diaphragm portion 162C includes a pair of plate portions 166Ca and 166Cb (second pair of plate portions) on a left-hand side. By overlapping with each other, the pair of plate portions 166Ca and 166Cb may form the left opening portion PC20 opposed to the second filter portion 142. That is, by changing the amount of overlapping of the pair of plate portions 165Ca and 165Cb on the right-hand side and the amount of overlapping of the pair of plate portions 166Ca and 166Cb on the left-hand side, the diaphragm mechanism 16C changes the size of the right opening portion PC10 and the left opening portion PC20 and adjusts the aperture value.

The pair of plate portions 165Ca and 165Cb on the right-hand side and the pair of plate portions 166Ca and 166Cb on the left-hand side constitute left and right areas of the pair of movable plates 164Ca and 164Cb, respectively. That is, the pair of plate portions 165Ca and 165Cb on the right-hand side are in a vertically symmetrical shape. The pair of plate portions 165Ca and 165Cb on the right-hand side are opposed to each other in the Y-axis direction. The pair of plate portions 166Ca and 166Cb on the left-hand side are in a vertically symmetrical shape. The pair of plate portions 165Ca and 165Cb on the left-hand side are opposed to each other in the Y-axis direction. The pair of plate portions 166Ca and 166Cb on the left-hand side have a horizontally symmetrical shape with respect to the pair of plate portions 165Ca and 165Cb on the right-hand side.

The movable plate 164Ca includes a main body 168Ca, a connection 168Cc, and frame portions F1, F2, and F3. The frame portions F1, F2, and F3 are arranged at a lower portion of the main body 168Ca. The frame portions F1, F2, and F3 constitute frames of a right opening portion PC10 and a left opening portion PC20. The connection 168Cc is located between the main body 168Ca and the frame portions F1, F2, and F3. The connection 168Cc connects the frame portions F1, F2, and F3 to the main body 168Ca.

The frame portion F1 constitutes a frame on an upper right side of the right opening portion PC10. The frame portion F1 is provided at a lower right portion of the main body 168Ca via the connection 168Cc. The frame portion F2 is provided in a boundary portion between the right opening portion PC10 and the left opening portion PC20. The frame portion F2 is provided at a lower center of the main body 168Ca via the connection 168Cc. The frame portion F3 constitutes a frame on an upper left side of the left opening portion PC20. The frame portion F3 is provided at a lower left portion of the main body 168Ca via the connection 168Cc. The shape and size of the frame portions F1, F2, and F3 may be set in view of the shape and the size of the opening portions. For example, such that the opening portion has a hexagonal shape, the frame portions F1 and F3 may be in an almost-right triangle shape and the frame portion F2 may be in a horizontally-symmetrical trapezoidal shape including corners with an angle of 60°.

The movable plate 164Cb may be vertically symmetrical with respect to the movable plate 164Ca. That is, the movable plate 164Cb includes a main body 168Cb, a connection 168Cd, and frame portions F4, F5, and F6. The frame portion F4 constitutes a frame on an upper right side of the right opening portion PC10. The frame portion F4 is provided at an upper right portion of the main body 168Cb. The frame portion F5 is provided in a boundary portion between the right opening portion PC10 and the left opening portion PC20 and provided at an upper center of the main body 168Cb. The frame portion F6 constitutes a frame on a lower left side of the left opening portion PC20 and provided at an upper left portion of the main body 168Cb.

Note that, right halves of the main bodies 168Ca and 168Cb, right halves of the frame portions F2 and F5, and the frame portions F1 and F4 constitute the pair of plate portions 165Ca and 165Cb on the right-hand side. Similarly, the left halves of the main bodies 168Ca and 168Cb, the left halves of the frame portions F2 and F5, and the frame portions F3 and F6 constitute the pair of plate portions 166Ca and 166Cb on the left hand side.

By moving the pair of movable plates 164Ca and 164Cb closer to or away from each other in the Y-axis direction, the mechanism portion (not shown) changes the amount of overlapping of the frame portions F1 to F6. With this, it becomes possible to adjust the size of the right opening portion PC10 and the left opening portion PC20.

For example, the mechanism portion may include a ball screw unit. The ball screw unit is connected to each of the pair of movable plates 164Ca and 164Cb. With this, the positions of the pair of movable plates 164Ca and 164Cb may be fixed at predetermined positions along the Y-axis direction. Further, the mechanism portion further includes an electric motor or the like as a ball screw driving source. With this, without directly touching the endoscope apparatus 100, the mechanism portion can be driven.

Here, as shown in FIG. 13A, the frame portions F1, F2, and F3 do not overlap with the frame portions F4, F5, and F6 in the case where a distance between the main bodies 168Ca and 168Cb in the Y-axis direction is equal to a predetermined distance or more. With this, the right opening portion PC10 and the left opening portion PC20 become a single large opening.

On the other hand, as shown in FIG. 13B, the frame portion F1 overlaps with the frame portion F4, the frame portion F2 overlaps with the frame portion F5, and the frame portion F3 overlaps with the frame portion F6 in the case where the distance between the main bodies 168Ca and 168Cb in the Y-axis direction is less than the predetermined distance. With this, the right opening portion PC10 and the left opening portion PC20 are formed to have a hexagonal shape. In addition, by changing the amount of overlapping, it becomes possible to change the opening area of the right opening portion PC10 and the left opening portion PC20.

Further, a distance between a gravity center CC10 (natural center or mass center) of the right opening portion PC10 and a gravity center CC20 (natural center or mass center) of the left opening portion PC20 is constantly maintained. That is because the diaphragm mechanism 16C according to this embodiment is configured to move the pair of movable plates 164Ca and 164Cb only in the Y-axis direction. That is, in the X-axis direction (left- and right-hand directions) in which the centers CC10 and CC20 are opposed to each other, only overlapping portions of the frame portions F1 to F6 are deformed, and hence the distance between the centers is maintained. Therefore, also with the endoscope apparatus 10C according to this embodiment, the baseline length D of the binocular disparity is constantly maintained. Thus, it becomes possible to change the aperture value and maintain the disparity between the right-eye image and the left-eye image.

The endoscope apparatus 100 according to this embodiment having the above-mentioned configuration includes the right opening portion PC10 and the left opening portion PC20 that varies in size only in the Y-axis direction. Therefore, it becomes possible to change the aperture value while maintaining the disparity in the X-axis direction. Further, by adjusting the amount of overlapping of the two movable plates 168Ca and 168Cb in the Y-axis direction, it is possible to continuously change the opening area of the right opening portion PC10 and the left opening portion PC20. With this, it becomes possible to finely adjust the aperture value and easily obtain a desired depth of field.

Fourth Embodiment

Figure 14:
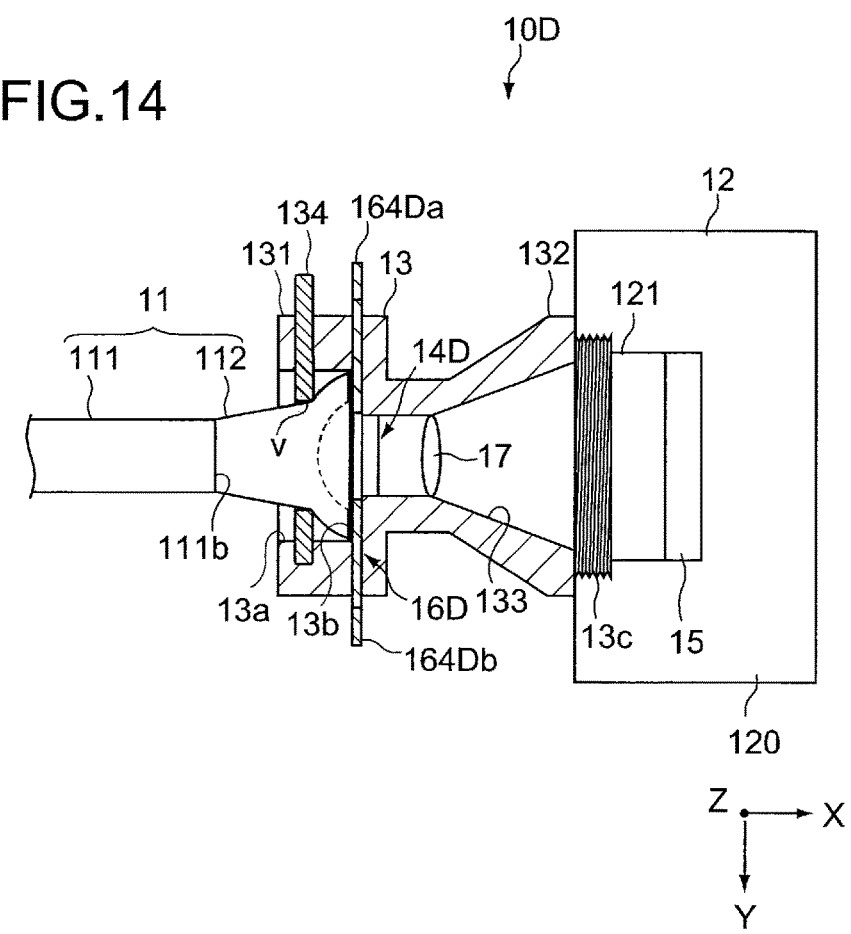
FIG. 14 is a schematic cross-sectional view showing a main-part configuration of an imaging apparatus according to a fourth embodiment of the present disclosure.

FIG. 14 is a schematic cross-sectional view showing a main-part configuration of an endoscope apparatus 10D according to a fourth embodiment of the present disclosure. Note that, in FIG. 14, parts corresponding to those of the above-mentioned first embodiment will be denoted by the same reference symbols and detailed description will be omitted or simplified.

This embodiment is different from the first embodiment in that a diaphragm mechanism 16D is provided not on a light-emitting side of a polarization filter 14D but on a light incident side of the polarization filter 14D.

The diaphragm mechanism 16D is provided at the end portion of the eyepiece 112 such that the diaphragm mechanism 16D is aligned with the reference surface 13b of the first connection end portion 131. On the other hand, the polarization filter 14D is installed in the adapter 13 and provided between the diaphragm mechanism 16D and the imaging lens 17. Note that, the diaphragm mechanism 16D may be provided adjacent to the polarization filter 14D or an insertion portion into which the diaphragm mechanism 16D is to be inserted may be formed in the adapter 13 as in the first embodiment.

The configuration of the diaphragm mechanism 16D is similar to that of the diaphragm mechanism 16 according to the first embodiment. That is, the first diaphragm portion 161 is opposed to the first filter portion 141 and the second diaphragm portion 162 is opposed to the second filter portion 142. Therefore, the first diaphragm portion 161 reduces image light of the right-eye image to obtain a predetermined aperture value and inputs the image light into the first filter portion 141. On the other hand, the second diaphragm portion 162 reduces image light of the left-eye image to obtain the predetermined aperture value and inputs the image light into the second filter portion 142.

Further, a distance between centers of the first opening pair P10 and the second opening pair P20 corresponds to the distance D between center positions of the first filter portion 141 and the second filter portion 142. With this, the right-eye image data and the left-eye image data can be generated from the first polarized light L1 passing through the first filter portion 141 of the polarization filter 14 and the second polarized light L2 passing through the second filter portion 142. Here, the baseline length of the binocular disparity between the right-eye image data and the left-eye image data is D.

Also with the endoscope apparatus 10D according to this embodiment, the same actions and effects as those in the above-mentioned first embodiment can be given.

Although the embodiments of the present disclosure have been described, the present disclosure is not limited only to the above-mentioned embodiments and various changes may be made without departing from the gist of the present disclosure.

Figure 15:
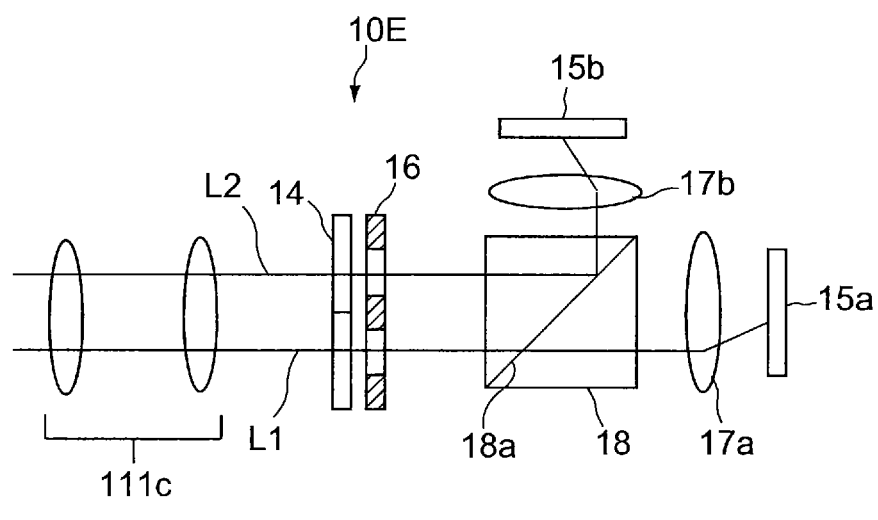
FIG. 15 is a schematic view showing one example of an optical system according to a modified example of the imaging apparatus according to the first embodiment of the present disclosure.

Although in the above-mentioned embodiments, the single image sensor 15 is used, the present disclosure is not limited thereto. For example, FIG. 15 is a schematic view showing, as a modified example of the first embodiment, a configuration example of an optical system of an endoscope apparatus 10E including two image sensors of a right-eye image sensor 15a and a left-eye image sensor 15b.

In this modified example, configurations of the imaging optical system 111c to the polarization filter 14 are the same as those of the first embodiment. However, this modified example is different from the first embodiment in that a beam splitter 18 is provided on the light-emitting side of the polarization filter 14. The beam splitter 18 is, for example, an almost rectangular shape. The beam splitter 18 includes a polarization and separation surface 18a in a diagonal direction. The polarization and separation surface 18a transmits first polarized light L1. The first polarized light L1 has a P-wave as a polarization component. The polarization and separation surface 18a reflects second polarized light L2 by 90°. The second polarized light L2 has an S-wave as a polarization component. With this, the first polarized light L1 and the second polarized light L2 are separated. The first polarized light L1 and the second polarized light L2 are inputted into the right-eye image sensor 15a and the left-eye image sensor 15b, respectively. Note that, as shown in FIG. 15, between the beam splitter 18 and the image sensors 15a and 15b, the imaging lenses 17a and 17b may be provided, respectively. Further, the configuration of the beam splitter 18 is not limited to the above-mentioned configuration of the first polarized light L1 (p-polarization component) and the second polarized light L2 (s-polarization component) may be separated.

In this modified example, the right-eye image data and the left-eye image data can be generated from the first polarized light L1 and the second polarized light L2 without providing wire grid polarizers in the light-receiving surfaces 150 of the image sensor 15. Therefore, the same actions and effects as those in the above-mentioned first embodiment may be achieved. Of course, in addition, this modified example may be applied to the second to fourth embodiments.

Further, in the above-mentioned embodiments, the plurality of openings having different opening areas or the opening portion having the opening area varied by the movable plates opposed to each other in the Y-axis direction are used as the first opening portion and the second opening portion. However, the present disclosure is not limited thereto. For example, the iris diaphragm capable of adjusting the opening area by the diaphragm blades may be used as each of the first opening portion and the second opening portion (see FIG. 11A to 11C). In this case, the first opening portion is constituted of a right-eye iris diaphragm and the second opening portion is constituted of a left-eye iris diaphragm. Also with such a configuration, it becomes possible to change the aperture value of the first polarized light L1 and the second polarized light L2. Further, the centers of those diaphragms are opposed to the gravity centers (natural centers or mass centers) of the first filter portion and the second filter portion in the Z-axis direction, and hence it is possible to maintain the baseline length of the binocular disparity.

For example, in the above-mentioned embodiments, the diaphragm mechanism 16 is configured to be movable with respect to the polarization filter 14 and the adapter 13. However, the present disclosure is not limited thereto. For example, the diaphragm mechanism 16 and the polarization filter 14 may be movable together. For example, the first filter portion 141 may be bonded to the first diaphragm portion 161 of the diaphragm mechanism 16 and the second filter portion 142 may be bonded to the second diaphragm portion 162. At this time, the first filter portion 141 is formed in the same shape as that of the first movable plate 165. The second filter portion 142 is formed in the same shape as that of the second movable plate 166. Also with such a configuration, it becomes possible to adjust the aperture value of the first polarized light L1 (image light for right-eye image) and the second polarized light L2 (image light for left-eye image) while maintaining the disparity.

For example, in the above-mentioned embodiments, the diaphragm mechanism may be configured to be driven manually by a user or by a driving source such as an electric motor and a cylinder. However, those driving sources may be connected to the control unit 20 and the like in a wireless or wired manner such that the driving sources can communicate with the control unit 20 and the like. With this, a person other than the user who operates the endoscope apparatus 10 can control the aperture value. Further, for example, even in the case of a user such as an operator who has sterilized hands from a hygiene standpoint and cannot directly touch the endoscope apparatus 10, the aperture value can be adjusted.

For example, in the above-mentioned embodiments, the example in which the imaging apparatus according to the present disclosure is applied to the endoscope apparatus to be used in medical practice has been described. However, the present disclosure is not limited thereto and the imaging apparatus according to the present disclosure may be applied to, for example, a microscope and an industrial endoscope.

It should be noted that the present disclosure may also take the following configurations:

(1) An imaging apparatus, including:
a lens barrel configured to transmit a subject light flux;
a polarization filter including
a first filter portion configured to transmit therethrough a first polarization component of the subject light flux and to block a second polarization component orthogonal to the first polarization component, and
a second filter portion configured to block the first polarization component of the subject light flux and to transmit therethrough the second polarization component, the second filter portion being adjacent to the first filter portion in a first axis direction, the polarization filter being provided on an optical path of the subject light flux;
an imaging unit including
an image sensor configured to receive the first polarization component and the second polarization component, the image sensor being provided to the lens barrel, the imaging unit being configured to generate first disparity image data from the first polarization component and to generate second disparity image data from the second polarization component; and
a diaphragm mechanism that is provided on the optical path of the subject light flux.

(2) The imaging apparatus according to Item (1), in which the diaphragm mechanism includes
a first diaphragm portion that is opposed to the first filter portion, and
a second diaphragm portion that is opposed to the second filter portion, the diaphragm mechanism being configured to change an aperture value of the first diaphragm portion and the second diaphragm portion while maintaining a disparity between the first disparity image and the second disparity image.

(3) The imaging apparatus according to Item (2), in which the first diaphragm portion includes
a first plate portion including a plurality of first opening portions having different opening areas,
the second diaphragm portion includes
a second plate portion including a plurality of second opening portions having different opening areas, and
the diaphragm mechanism further includes
a mechanism portion configured to support the first plate portion and the second plate portion to be movable such that any one of the plurality of first opening portions is opposed to the first filter portion and any one of the plurality of second opening portions is opposed to the second filter portion.

(4) The imaging apparatus according to Item (3), in which the first plate portion and the second plate portion are integrally formed.

(5) The imaging apparatus according to Item (3) or (4), in which
the plurality of first opening portions and the plurality of second opening portions are spaced from each other in the first axis direction and arranged along the second axis direction in the first plate portion and the second plate portion, respectively, the second axis direction being orthogonal to the first axis direction, and
the mechanism portion is configured to move the first plate portion and the second plate portion along the second axis direction.

(6) The imaging apparatus according to Item (3) or (4), in which
the plurality of first opening portions are arranged along a first circumference in the first plate portion,
the plurality of second opening portions are arranged along a second circumference in the second plate portion, the second circumference being concentric with the first circumference, and the mechanism portion is configured to move the first plate portion and the second plate portion along the first circumference and the second circumference, respectively.

(7) The imaging apparatus according to Item (2), in which the first diaphragm portion includes a first pair of plate portions capable of overlapping with each other to form a first opening portion opposed to the first filter portion, the second diaphragm portion includes a second pair of plate portions capable of overlapping with each other to form a second opening portion opposed to the second filter portion, and the diaphragm mechanism further includes a mechanism portion configured to change the amount of overlapping of the first pair of plate portions and the second pair of plate portions such that a size of the first opening portion and the second opening portion is adjusted.

(8) The imaging apparatus according to any one of Items (1) to (7), in which the diaphragm mechanism is provided adjacent to the polarization filter.

(9) The imaging apparatus according to any one of Items (1) to (8), in which the diaphragm mechanism is provided on a light-emitting side of the polarization filter.

(10) The imaging apparatus according to any one of Items (1) to (9), in which the diaphragm mechanism is provided on a light incident side of the polarization filter.

(11) The imaging apparatus according to any one of Items (1) to (10), in which the image sensor includes a light-receiving surface including a plurality of first polarizers configured to transmit therethrough the first polarization component and block the second polarization component, and a plurality of second polarizers configured to block the first polarization component and transmit therethrough the second polarization component, the plurality of first polarizers and the plurality of second polarizers being arranged in a matrix form.

(12) An optical device for stereoscopic imaging, including:

an aperture unit configured to adjust an aperture value of first and second aperture portions while maintaining a binocular disparity between a first alignment location of the first aperture portion and a second alignment location of the second aperture portion.

(13) The optical device of Item (1), wherein the aperture unit includes:

a plurality of pairs of the first and the second aperture portions, each pair configured to correspond to a different aperture value, each pair configured to be placed within an optical path to adjust the aperture value to the different aperture value that corresponds to that pair.

(14) The optical device of Item (13), wherein each pair of the first and the second apertures includes:

a polarization filter configured to include first and second filter portions that include a respective first and second mass center, the first filter portion contained within the first aperture portion and the second filter portion contained within the second aperture portion, the first mass center corresponding with the first alignment location and the second mass center corresponding to a second alignment location.

(15) The optical device of Item (13), wherein the aperture unit includes:

a diaphragm mechanism configured to include the plurality of pairs of the first and the second aperture portions, the diaphragm mechanism being configured to move in a direction orthogonal to the optical path.

(16) The optical device of Item (14), wherein the diaphragm mechanism is a plate configured to slide in a direction orthogonal to the optical path.

(17) The optical device of item (14), wherein the diaphragm mechanism is a disk configured to rotate around an axis parallel to the optical path.

(18) The optical device of Item (12), wherein the aperture unit includes a diaphragm mechanism configured to include:

a pair of movable plates configured to slide along a direction orthogonal to the optical path in opposite directions, wherein the aperture value of the first and the second aperture portions is adjusted based on a position of the pair of movable plates.

(19) The optical device of Item (12), wherein the aperture unit includes a diaphragm mechanism configured to include:

a pair of iris diaphragms, wherein the aperture value of the first and the second aperture portions is adjusted based on a variable position of the pair of iris diaphragms.

(20) The optical device of Item (12), wherein the optical device includes:

a polarization filter configured to include first and second filter portions that include a respective first and second mass center, the first mass center corresponding with the first alignment location and the second mass center corresponding to a second alignment location.

(21) The optical device of Item (20), wherein the polarization filter is configured on an object side of the aperture unit.

(22) The optical device of Item (20), wherein the polarization filter is configured on an image side of the aperture unit.

(23) An endoscope apparatus including:

a lens barrel;

an imaging part; and an optical device for stereoscopic imaging, including:

an aperture unit configured to adjust an aperture value of first and second aperture portions while maintaining a binocular disparity between a first alignment location of the first aperture portion and a second alignment location of the second aperture portion.

What is claimed is:

1. An optical device comprising:

a single lens chain for stereoscopic imaging; and a diaphragm mechanism including a first diaphragm portion and a second diaphragm portion, the first diaphragm portion including a first circular aperture portion with a first alignment location, the second diaphragm portion including a second circular aperture portion with a second alignment location, and the diaphragm mechanism configured to adjust an aperture value of the first diaphragm portion and the second diaphragm portion, and maintain a binocular disparity between the first alignment location and the second alignment location; and a polarization filter including a first filter portion and a second filter portion, the first filter portion including a first mass center that is positioned to correspond with the first alignment location, and the second filter portion including a second mass center that is positioned to correspond with the second alignment location, wherein, to maintain the binocular disparity between the first alignment location of the first circular aperture portion of the first diaphragm portion and the second alignment location of the second circular aperture portion of the second diaphragm portion, the diaphragm mechanism is further configured to maintain a distance between a first mass center axis of the first mass center and a second mass center axis of the second mass center.

2. The optical device of claim 1, wherein the diaphragm mechanism includes:
   a plurality of circular aperture portions including the first circular aperture portion, the second circular aperture portion, a third circular aperture portion, a fourth circular aperture portion, a fifth circular aperture portion, and a sixth circular aperture portion,
   wherein the first circular aperture portion and the second circular aperture portion are a first circular aperture pair having a first aperture value,
   wherein the third circular aperture portion and the fourth circular aperture portion are a second circular aperture pair having a second aperture value,
   wherein the fifth circular aperture portion and the sixth circular aperture portion are a third circular aperture pair having a third aperture value,
   wherein the first aperture value, the second aperture value, and the third aperture value are different from each other, and
   wherein each of the first aperture pair, the second aperture pair, and the third aperture pair is configured to be placed within an optical path to adjust the aperture value to a corresponding value.

3. The optical device of claim 2, wherein the first aperture pair includes:
   the polarization filter,
   wherein the first filter portion is contained within the first circular aperture portion, and
   wherein the second filter portion contained is within the second circular aperture portion.

4. The optical device of claim 2, wherein the diaphragm mechanism is configured to move in a direction orthogonal to the optical path.

5. The optical device of claim 3, wherein the diaphragm mechanism is a plate configured to slide in a direction orthogonal to the optical path.

6. The optical device of claim 3, wherein the diaphragm mechanism is a disk configured to rotate around an axis parallel to the optical path.

7. The optical device of claim 1, wherein the diaphragm mechanism includes
   movable plates configured to slide along a direction orthogonal to an optical path in opposite directions relative to each other, wherein the aperture value of the first circular aperture portion and the second circular aperture portion is adjusted based on a position of the movable plates.

8. The optical device of claim 1, wherein the diaphragm mechanism includes
   iris diaphragms, wherein the aperture value of the first circular aperture portion and the second circular aperture portion is adjusted based on a variable position of each of the iris diaphragms.

9. The optical device of claim 1, further comprising: an optic system including at least one relay lens that is configured to transmit light to the diaphragm mechanism.

10. An endoscope apparatus comprising:
    a lens barrel;
    an imaging part; and
    an optical device having
        a single chain lens for stereoscopic imaging, and
        a diaphragm mechanism including a first diaphragm portion and a second diaphragm portion, the first diaphragm portion including a first circular aperture portion with a first alignment location, the second diaphragm portion including a second circular aperture portion with a second alignment location, and the diaphragm mechanism configured to
            adjust an aperture value of the first diaphragm portion and the second diaphragm portion, and
            maintain a binocular disparity between the first alignment location of the first circular aperture portion of the first diaphragm portion and the second alignment location of the second circular aperture portion of the second diaphragm portion; and
        a polarization filter including a first filter portion and a second filter portion, the first filter portion includes a first mass center that is positioned to correspond with the first alignment location, and the second filter portion includes a second mass center that is positioned to correspond with the second alignment location,
    wherein, to maintain the binocular disparity between the first alignment location of the first circular aperture portion of the first diaphragm portion and the second alignment location of the second circular aperture portion of the second diaphragm portion,
        the diaphragm mechanism is further configured to maintain a distance between a first mass center axis of the first mass center and a second mass center axis of the second mass center.

11. The endoscope apparatus of claim 10, wherein the diaphragm mechanism includes:
    a plurality of circular aperture portions including the first circular aperture portion, the second circular aperture portion, a third circular aperture portion, a fourth circular aperture portion, a fifth circular aperture portion, and a sixth circular aperture portion,
    wherein the first circular aperture portion and the second circular aperture portion are a first circular aperture pair having a first aperture value,
    wherein the third circular aperture portion and the fourth circular aperture portion are a second circular aperture pair having a second aperture value,
    wherein the fifth circular aperture portion and the sixth circular aperture portion are a third circular aperture pair having a third aperture value,
    wherein the first aperture value, the second aperture value, and the third aperture value are different from each other, and
    wherein each of the first aperture pair, the second aperture pair, and the third aperture pair is configured to be placed within an optical path to adjust the aperture value to a corresponding value.

12. The endoscope apparatus of claim 11, wherein the first aperture pair includes:
    the polarization filter,
    wherein the first filter portion is contained within the first circular aperture portion, and
    wherein the second filter portion is contained within the second circular aperture portion.

13. The endoscope apparatus of claim 11, wherein the diaphragm mechanism is configured to move in a direction orthogonal to the optical path.

14. The endoscope apparatus of claim 12, wherein the diaphragm mechanism is a plate configured to slide in a direction orthogonal to the optical path.

15. The endoscope apparatus of claim 10, wherein the diaphragm mechanism includes iris diaphragms, wherein the aperture value of the first circular aperture portion and the second circular aperture portion is adjusted based on a variable position of each of the iris diaphragms.

16. The optical device according to claim 1, further comprising:
an optic system including at least one lens that is configured to transmit light to the diaphragm mechanism,
wherein the diaphragm mechanism and the optic system are arranged such that mass center axes of the first mass center and the second mass center are different from an optical axis of incident light directed to the diaphragm mechanism.

17. The optical device according to claim 1, wherein the second filter portion is positioned to the right of the first filter portion along an X-axis.

* * * * *